(12) United States Patent
Truckai et al.

(10) Patent No.: US 7,041,102 B2
(45) Date of Patent: May 9, 2006

(54) ELECTROSURGICAL WORKING END WITH REPLACEABLE CARTRIDGES

(75) Inventors: Csaba Truckai, Saratoga, CA (US); James A. Baker, Palo Alto, CA (US); Gabor Gran, San Jose, CA (US); John H. Shadduck, Tiburon, CA (US)

(73) Assignee: SurgRx, Inc., Palo Alto, CA (US)

( * ) Notice: Subject to any disclaimer, the term of this patent is extended or adjusted under 35 U.S.C. 154(b) by 0 days.

(21) Appl. No.: 10/443,974

(22) Filed: May 22, 2003

(65) Prior Publication Data

US 2003/0220637 A1 Nov. 27, 2003

Related U.S. Application Data

(63) Continuation-in-part of application No. 10/032,867, filed on Oct. 22, 2001, now Pat. No. 6,929,644.

(60) Provisional application No. 60/362,689, filed on May 23, 2002.

(51) Int. Cl.
*A61B 18/12* (2006.01)

(52) U.S. Cl. .......................... 606/51; 606/49
(58) Field of Classification Search .............. 606/41–52
See application file for complete search history.

(56) References Cited

U.S. PATENT DOCUMENTS

| | | | |
|---|---|---|---|
| 659,409 A | 10/1900 | Mosher | |
| 1,586,645 A | 6/1926 | Bierman | |
| 1,798,902 A | 3/1931 | Raney | |
| 1,881,250 A | 10/1932 | Tomlinson | |
| 2,031,682 A | 2/1936 | Wappler et al. | |
| 3,651,811 A | 3/1972 | Hildebrandt et al. | |
| 3,685,518 A | 8/1972 | Beuerle et al. | |
| 3,730,188 A | 5/1973 | Ellman | |
| 3,768,482 A | 10/1973 | Shaw | |
| 3,826,263 A | 7/1974 | Cage et al. | |
| 4,092,986 A | 6/1978 | Schneiderman | |
| 4,198,957 A | 4/1980 | Cage et al. | |
| 4,219,025 A | 8/1980 | Johnson | |
| 4,231,371 A | 11/1980 | Lipp | |
| 4,232,676 A | 11/1980 | Herczog | |
| 4,271,838 A | 6/1981 | Lasner et al. | |
| 4,353,371 A | 10/1982 | Cosman | |
| 4,370,980 A | 2/1983 | Lottick | |
| 4,375,218 A | 3/1983 | DiGeronimo | |

(Continued)

FOREIGN PATENT DOCUMENTS

EP  341 446 A2  4/1989

(Continued)

OTHER PUBLICATIONS

Corson, S.L., "Two new laparoscopic instruments: Bipolar sterilizing forceps and uterine manipulator," *Medical Instrumentation*, 11(1):7-8 (1977).

(Continued)

*Primary Examiner*—Roy D. Gibson
*Assistant Examiner*—Aaron Roane
(74) *Attorney, Agent, or Firm*—Townsend and Townsend and Crew LLP.

(57) ABSTRACT

An electrosurgical medical device and method for creating thermal welds in engaged tissue that carries the electrosurgical components in a disposable cartridge. The instrument also can carry a blade member in a disposable cartridge, thus making the instrument system inexpensive to use. In another embodiment, the electrical leads of the cartridge have a surface coating of a thermochromic material to provide the physician with a visual indicator of operational parameters when applying energy to tissue.

8 Claims, 34 Drawing Sheets

U.S. PATENT DOCUMENTS

| | | |
|---|---|---|
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A * | 9/1995 | Goble et al. .................. 606/48 |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A * | 2/1998 | Yates .......................... 606/139 |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschal et al. |
| 5,800,449 A | 9/1998 | Wales |
| 5,807,392 A | 9/1998 | Eggers |
| 5,833,690 A | 11/1998 | Yates et al. |
| 5,911,719 A | 6/1999 | Eggers |
| 5,947,984 A | 9/1999 | Whipple |
| 6,019,758 A | 2/2000 | Slater |
| 6,039,733 A | 3/2000 | Buysse et al. |
| 6,074,389 A | 6/2000 | Levine et al. |
| 6,086,586 A | 7/2000 | Hooven |
| 6,113,598 A | 9/2000 | Baker |
| H001904 H * | 10/2000 | Yates et al. .................... 606/50 |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,218,928 B1 * | 4/2001 | Okada et al. ............. 338/22 R |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,296,640 B1 | 10/2001 | Wampler et al. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B1 | 10/2002 | Schmaltz |
| 6,468,275 B1 | 10/2002 | Wampler et al. |
| 6,492,629 B1 * | 12/2002 | Sopory ....................... 219/535 |
| 6,500,176 B1 | 12/2002 | Truckai et al. |
| 6,511,480 B1 | 1/2003 | Tetzlaff et al. |
| 6,533,784 B1 | 3/2003 | Truckai et al. |
| 6,554,829 B1 | 4/2003 | Schulze et al. |
| 6,575,968 B1 | 6/2003 | Eggers et al. |
| 6,585,735 B1 | 7/2003 | Frazier et al. |
| 6,632,193 B1 | 10/2003 | Davison et al. |
| 6,652,521 B1 | 11/2003 | Schulze |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

FOREIGN PATENT DOCUMENTS

| | | |
|---|---|---|
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 342617 | 7/1972 |
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New Inventions" *The Lancet*, pp. 650-651 (1959).

Nardella, P.C., "Radio Frequency Energy and Impedance Feedback," *Proc. SPIE. Catheter-Based Sensing and Imaging Technology*, 1068: 42-48 (1989).

Vallfors et al., "Automatically controlled bipolar electrocoagulation—'COA-COMP'," *Neurosurg Rev.*, 187-190 (1984).

* cited by examiner

ELECTROSURGICAL WORKING END WITH REPLACEABLE CARTRIDGES

CROSS-REFERENCE TO RELATED APPLICATIONS

This application claims benefit from Provisional U.S. patent application Ser. No. 60/362,689 filed May 23, 2002 having the same title as above, which application is incorporated herein by this reference. This application is a Continuation-In-Part of U.S. patent application Ser. No. 10/032,867 filed Oct. 22, 2001, now issued as U.S. Pat. No. 6,929,644, titled Electrosurgical Jaw Structure for Controlled Energy Delivery.

BACKGROUND OF THE INVENTION

1. Field of the Invention

This invention relates to medical devices and techniques and more particularly relates to an electrosurgical system that can apply energy to tissue from an engagement surface that modulates the Rf power levels applied to tissue across micron-scale portions of the engagement surface, together with means for providing the electrosurgical functionality in a disposable cartridge.

2. Description of the Related Art

In the prior art, various energy sources such as radiofrequency (Rf) sources, ultrasound sources and lasers have been developed to coagulate, seal or join together tissues volumes in open and laparoscopic surgeries. The most important surgical application relates to sealing blood vessels which contain considerable fluid pressure therein. In general, no instrument working ends using any energy source have proven reliable in creating a "tissue weld" or "tissue fusion" that has very high strength immediately post-treatment. For this reason, the commercially available instruments, typically powered by Rf or ultrasound, are mostly limited to use in sealing small blood vessels and tissues masses With microvasculature therein. The prior art Rf devices also fail to provide seals with substantial strength in anatomic structures having walls with irregular or thick fibrous content, in bundles of disparate anatomic structures, in substantially thick anatomic structures, or in tissues with thick fascia layers (e.g., large diameter blood vessels).

In a basic bi-polar Rf jaw arrangement, each face of opposing first and second jaws comprises an electrode and Rf current flows across the captured tissue between the opposing polarity electrodes. Such prior art Rf jaws that engage opposing sides of tissue typically cannot cause uniform thermal effects in the tissue—whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art Rf jaws can cause further undesirable effects by propagating Rf density laterally from the engaged tissue thus causing unwanted collateral thermal damage.

The commercially available Rf sealing instruments typically use one of two approaches to "control" Rf energy delivery in tissue. In a first "power adjustment" approach, the Rf system controller can rapidly adjust the level of total power delivered to the jaws' engagement surfaces in response to feedback circuitry coupled to the active electrodes that measures tissue impedance or electrode temperature. In a second "current-path directing" approach, the instrument jaws carry an electrode arrangement in which opposing polarity electrodes are spaced apart by an insulator material—which may cause current to flow within an extended path through captured tissue rather that simply between surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848 and 5,833,690.

The illustrations of the wall of a blood vessel in FIGS. 1A–1D are useful in understanding the limitations of prior art Rf working ends for sealing tissue. FIG. 1B provides a graphic illustration of the opposing vessel walls portions 2a and 2b with the tissue divided into a grid with arbitrary micron dimensions—for example, the grid can represent 5 microns on each side of the targeted tissue. In order to create the most effective "weld" in tissue, each micron-dimensioned volume of tissue must be simultaneously elevated to the temperature needed to denature proteins therein. As will be described in more detail below, in order to create a "weld" in tissue, collagen, elastin and other protein molecules within an engaged tissue volume must be denatured by breaking the inter- and intra-molecular hydrogen bonds—followed by re-crosslinking on thermal relaxation to create a fused-together tissue mass. It can be easily understood that ohmic heating in tissue-if not uniform—can at best create localized spots of truly "welded" tissue. Such a non-uniformly denatured tissue volume still is "coagulated" and will prevent blood flow in small vasculature that contains little pressure. However, such non-uniformly denatured tissue will not create a seal with significant strength, for example in 2 mm. to 10 mm. arteries that contain high pressures.

Now turning to FIG. 1C, it is reasonable to ask whether the "power adjustment" approach to energy delivery is likely to cause a uniform temperature within every micron-scale tissue volume in the grid simultaneously—and maintain that temperature for a selected time interval. FIG. 1C shows the opposing vessel walls 2a and 2b being compressed with cut-away phantom views of opposing polarity electrodes on either side of the tissue. One advantage of such an electrode arrangement is that 100% of each jaw engagement surface comprises an "active" conductor of electrical current—thus no tissue is engaged by an insulator which theoretically would cause a dead spot (no ohmic heating) proximate to the insulator. FIG. 1C graphically depicts current "paths" p in the tissue at an arbitrary time interval that can be microseconds ($\mu$s) apart. Such current paths p would be random and constantly in flux—along transient most conductive pathways through the tissue between the opposing polarity electrodes. The thickness of the "paths" is intended to represent the constantly adjusting power levels. If one assumes that the duration of energy density along any current path p is within the microsecond range before finding a new conductive path—and the thermal relaxation time of tissue is the millisecond (ms) range, then what is the likelihood that such entirely random current paths will revisit and maintain each discrete micron-scale tissue volume at the targeted temperature before thermal relaxation? Since the hydration of tissue is constantly reduced during ohmic heating—any regions of more desiccated tissue will necessarily lose its ohmic heating and will be unable to be "welded" to adjacent tissue volumes. The "power adjustment" approach probably is useful in preventing rapid overall tissue desiccation. However, it is postulated that any approach that relies on entirely "random" current paths p in tissue—no matter the power level—cannot cause contemporaneous denaturation of tissue constituents in all engaged tissue volumes and thus cannot create an effective high-strength "weld" in tissue.

Now referring to FIG. 1D, it is possible to evaluate the second "current-path directing" approach to energy delivery in a jaw structure. FIG. 1D depicts vessel walls 2a and 2b engaged between opposing jaws surfaces with cutaway phantom views of opposing polarity (+) and (−) electrodes on each side of the engaged tissue. An insulator indicated at 10 is shown in cut-away view that electrically isolates the electrodes in the jaw. One significant disadvantage of using an insulator 10 in a jaw engagement surface is that no ohmic heating of tissue can be delivered directly to the tissue volume engaged by the insulator 10 (see FIG. 1D). The tissue that directly contacts the insulator 10 will only be ohmically heated when a current path p extends through the tissue between the spaced apart electrodes. FIG. 1D graphically depicts current paths p at any arbitrary time interval, for example in the µs range. Again, such current paths p will be random and in constant flux along transient conductive pathways.

This type of random, transient Rf energy density in paths p through tissue, when any path may occur only for a microsecond interval, is not likely to uniformly denature proteins in the entire engaged tissue volume. It is believed that the "current-path directing" approach for tissue sealing can only accomplish tissue coagulation or seals with limited strength.

Now turning to FIG. 2, it can be conceptually understood that the key requirements for thermally-induced tissue welding relate to: (i) means for "non-random spatial localization" of energy densities in the engaged tissue et, (ii) means for "controlled, timed intervals" of power application of such spatially localized of energy densities, and (iii) means for "modulating the power level " of any such localized, time-controlled applications of energy.

FIG. 2 illustrates a hypothetical tissue volume with a lower jaw's engagement surface 15 backed away from the tissue. The tissue is engaged under very high compression which is indicated by arrows in FIG. 2. The engagement surface 15 is shown as divided into a hypothetical grid of "pixels" or micron-dimensioned surface areas 20. Thus, FIG. 2 graphically illustrates that to create an effective tissue weld, the delivery of energy should be controlled and non-randomly spatially localized relative to each pixel 20 of the engagement surface 15.

Still referring to FIG. 2, it can be understood that there are two modalities in which spatially localized, time-controlled energy applications can create a uniform energy density in tissue for protein denaturation. In a first modality, all cubic microns of the engaged tissue (FIG. 2) can be elevated to the required energy density and temperature contemporaneously to create a weld. In a second modality, a "wave" of the required energy density can sweep across the engaged tissue et that can thereby leave welded tissue in its wake. The authors have investigated, developed and integrated Rf systems for accomplishing both such modalities—which are summarized in the next Section.

SUMMARY OF THE INVENTION

The systems and methods corresponding to invention relate to creating thermal "welds" or "fusion" within native tissue volumes. The alternative terms of tissue "welding" and tissue "fusion" are used interchangeably herein to describe thermal treatments of a targeted tissue volume that result in a substantially uniform fused-together tissue mass that provides substantial tensile strength immediately post-treatment. Such tensile strength (no matter how measured) is particularly important (i) for welding blood vessels in vessel transection procedures, (ii) for welding organ margins in resection procedures, (iii) for welding other anatomic ducts wherein permanent closure is required, and also (iv) for vessel anastomosis, vessel closure or other procedures that join together anatomic structures or portions thereof.

The systems of the invention are useful for both endoscopic and open surgeries. In one embodiment, a re-useable scissor-type instrument can be provided with the electrosurgical component offered as a disposable cartridge. In one embodiment, the electrical lead of the cartridge has a surface coating of a thermochromic material to provide the physician with a visual indicator of operational parameters when applying energy to tissue. The instrument also can carry a blade member in a disposable cartridge, thus making the instrument system inexpensive to use.

The welding or fusion of tissue as disclosed herein is to be distinguished from "coagulation", "sealing", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the affected tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen, elastin and other protein molecules in a targeted tissue volume to create a transient liquid or gel-like proteinaceous amalgam. A selected energy density is provided in the targeted tissue to cause hydro-thermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in "protein entanglement" as re-crosslinking or renaturation occurs to thereby cause a uniform fused-together mass.

To better appreciate the scale at which thermally-induced protein denaturation occurs—and at which the desired protein entanglement and re-crosslinking follows—consider that a collagen molecule in its native state has a diameter of about 15 Angstroms. The collagen molecule consists of a triple helix of peptide stands about 1000 Angstroms in length (see FIG. 2). In other words—a single $\mu m^3$ (cubic micrometer) of tissue that is targeted for welding will contain 10's of thousands of such collagen molecules. In FIG. 2, each tissue volume in the grid represents an arbitrary size from about 1 µm to 5 µm (microns). Elastin and other molecules fro denaturation are believed to be similar in dimension to collagen.

To weld tissue, or more specifically to thermally-induce protein denaturation, and subsequent entanglement and re-crosslinking in a targeted tissue volume, it has been learned that the following interlinked parameters must be controlled:

(i) Temperature of thermal denaturation. The targeted tissue volume must be elevated to the temperature of thermal denaturation, $T_d$, which ranges from about 50° C. to 90° C., and more specifically is from about 60° C. to 80° C. The optimal $T_d$ within the larger temperature range is further dependent on the duration of thermal effects and level of pressure applied to the engaged tissue.

(ii) Duration of treatment. The thermal treatment must extend over a selected time duration, which depending on the engaged tissue volume, can range from less than 0.1 second to about 5 seconds. As will be described below, the system of the in invention utilizes a thermal treatment duration ranging from about 500 ms second to about 3000 ms. Since the objectives of protein entanglement occur at $T_d$ which can be achieved in ms (or even microseconds)—this disclosure will generally describe the treatment duration in ms.

(iii) Ramp-up in temperature; uniformity of temperature profile. There is no limit to the speed at which temperature can be ramped up within the targeted tissue. However, it is of utmost importance to maintain a very uniform temperature across the targeted tissue volume so that "all" proteins are denatured within the same microsecond interval. Only thermal relaxation from a uniform temperature $T_d$ can result in complete protein entanglement and re-crosslinking across an entire tissue volume. Without such uniformity of temperature ramp-up and relaxation, the treated tissue will not become a fused-together tissue mass—and thus will not have the desired strength.

Stated another way, it is necessary to deposit enough energy into the targeted volume to elevate it to the desired temperature $T_d$ before it diffuses into adjacent tissue volumes. The process of heat diffusion describes a process of conduction and convection and defines a targeted volume's thermal relaxation time (often defined as the time over which the temperature is reduced by one-half). Such thermal relaxation time scales with the square of the diameter of the treated volume in a spherical volume, decreasing as the diameter decreases. In general, tissue is considered to have a thermal relaxation time in the range of 1 ms. In a non-compressed tissue volume, or lightly compressed tissue volume, the thermal relaxation of tissue in an Rf application typically will prevent a uniform weld since the random current paths result in very uneven ohmic heating (see FIGS. 1C–1D).

(iv) Instrument engagement surfaces. The instrument's engagement surface(s) must have characteristics that insure that every square micron of the instrument surface is in contact with tissue during Rf energy application. Any air gap between an engagement surface and tissue can cause an arc of electrical energy across the insulative gap thus resulting in charring of tissue. Such charring (desiccation) will entirely prevent welding of the localized tissue volume and result in further collateral effects that will weaken any attempted weld. For this reason, the engagement surfaces corresponding to the invention are (i) substantially smooth at a macroscale, and (ii) at least partly of an elastomeric matrix that can conform to the tissue surface dynamically during treatment. The jaw structure of the invention typically has gripping elements that are lateral from the energy-delivering engagement surfaces. Gripping serrations otherwise can cause unwanted "gaps" and microscale trapped air pockets between the tissue and the engagement surfaces.

(v) Pressure. It has been found that very high external mechanical pressures on a targeted tissue volume are critical in welding tissue—for example, between the engagement surfaces of a jaw structure. In one aspect, as described above, the high compressive forces can cause the denatured proteins to be crushed together thereby facilitating the intermixing or intercalation of denatured protein stands which ultimately will result in a high degree of cross-linking upon thermal relaxation.

In another aspect, the proposed high compressive forces (it is believed) can increase the thermal relaxation time of the engaged tissue practically by an infinite amount. With the engaged tissue highly compressed to the dimension of a membrane between opposing engagement surfaces, for example to a thickness of about 0.001", there is effectively little "captured" tissue within which thermal diffusion can take place. Further, the very thin tissue cross-section at the margins of the engaged tissue prevents heat conduction to tissue volumes outside the jaw structure.

In yet another aspect, the high compressive forces at first cause the lateral migration of fluids from the engaged tissue which assists in the subsequent welding process. It has been found that highly hydrated tissues are not necessary in tissue welding. What is important is maintaining the targeted tissue at a selected level without desiccation as is typical in the prior art. Further, the very high compressive forces cause an even distribution of hydration across the engaged tissue volume prior to energy delivery.

In yet another aspect, the high compressive forces insure that the engagement planes of the jaws are in complete contact with the surfaces of the targeted tissues, thus preventing any possibility of an arc of electrical energy a cross a "gap" would cause tissue charring, as described previously.

One exemplary embodiment disclosed herein is particularly adapted for, in effect, independent spatial localization and modulation of Rf energy application across micron-scale "pixels" of an engagement surface. The jaw structure of the instrument defines opposing engagement planes that apply high mechanical compression to the engaged tissue. At least one engagement plane has a surface layer that comprises first and second portions of a conductive-resistive matrix—preferably including an elastomer such as silicone (first portion) and conductive particles (second portion) distributed therein. An electrical source is coupled to the working end such that the combination of the conductive-resistive matrix and the engaged tissue are intermediate opposing conductors that define first and second polarities of the electrical source coupled thereto. The conductive-resistive matrix is designed to exhibit unique resistance vs. temperature characteristics, wherein the matrix maintains a low base resistance over a selected temperature range with a dramatically increasing resistance above a selected narrow temperature range.

In operation, it can be understood that current flow through the conductive-resistive matrix and engagement plane will apply active Rf energy (ohmic heating) to the engaged tissue until the point in time that any portion of the matrix is heated to a range that substantially reduces its conductance. This effect will occur across the surface of the matrix thus allowing each matrix portion to deliver an independent level of power therethrough. This instant, localized reduction of Rf energy application can be relied on to prevent any substantial dehydration of tissue proximate to the engagement plane. The system eliminates the possibility of desiccation thus meeting another of the several parameters described above.

The conductive-resistive matrix and jaw body corresponding to the invention further can provides a suitable cross-section and mass for providing substantial heat capacity. Thus, when the matrix is elevated in temperature to the selected thermal treatment range, the retained heat of the matrix volume can effectively apply thermal energy to the engaged tissue volume by means of conduction and convection. In operation, the working end can automatically modulate the application of energy to tissue between active Rf heating and passive conductive heating of the targeted tissue to maintain a targeted temperature level.

Of particular interest, another system embodiment disclosed herein is adapted for causing a "wave" of ohmic heating to sweep across tissue to denature tissue constituents in its wake. This embodiment again utilizes at least one engagement plane in a jaw structure that carries a conductive-resistive matrix as described previously. At least one of the opposing polarity conductors has a portion thereof exposed in the engagement plane. The conductive-resistive matrix again is intermediate the opposing polarity conductors. When power delivery is initiated, the matrix defines an "interface" therein where microcurrents are most intense about the interface of the two polarities—since the matrix is not a simple conductor. The engaged tissue, in effect, becomes an extension of the interface of microcurrents created by the matrix—which thus localizes ohmic heating across the tissue proximate the interface. The interface of polarities and microcurrents within the matrix will be in flux due to lesser conductance about the interface as the matrix is elevated in temperature. Thus, a "wave-like" zone of microcurrents between the polarities will propagate across the matrix—and across the engaged tissue. By this means of engaging tissue with a conductive-resistive matrix, a wave of energy density can be caused to sweep across tissue to uniformly denature proteins which will then re-crosslink to create a uniquely strong weld.

In general, the system of conductive-resistive matrices for Rf energy delivery advantageously provides means for spatial-localization and modulation, of energy application from selected, discrete locations across a single energy-emitting surface coupled to a single energy source The system of conductive-resistive matrices for Rf energy delivery provides means for causing a dynamic wave of ohmic heating in tissue to propagate across engaged tissue.

The system of conductive-resistive matrices for Rf energy delivery allows for opposing electrical potentials to be exposed in a single engagement surface with a conductive matrix therebetween to allow 100% of the engagement surface to emit energy to tissue.

The system of conductive-resistive matrices for Rf energy application to tissue allows for bi-polar electrical potential to be exposed in a single engagement surface without an intermediate insulator portion.

The system of conductive-resistive matrices for energy delivery allows for the automatic modulation of active ohmic heating and passive heating by conduction and convection to treat tissue.

The system of conductive-resistive matrices for energy application to tissue advantageously allows for the creation of "welds" in tissue within about 500 ms to 2 seconds.

The system of conductive-resistive matrices for energy application to tissue provides "welds" in blood vessels that have very high strength.

Additional objects and advantages of the invention will be apparent from the following description, the accompanying drawings and the appended claims.

BRIEF DESCRIPTION OF THE DRAWINGS

FIG. 14A being the engagement surface of FIG. 12 engaging tissue membrane at the time that energy delivery is initiated causing localized microcurrents and ohmic tissue heating;

FIG. 14B being the engagement surface of FIG. 12 after an arbitrary millisecond or microsecond time interval depicting the propagation of a wavefronts of energy outward from the initial localized microcurrents as the localized temperature and resistance of the matrix is increased; and FIG. 14C being the engagement surface of FIG. 12 after another very brief interval depicting the propagation of the wavefronts of energy density outwardly in the tissue due to increase temperature and resistance of matrix portions.

FIG. 18A corresponding to the view of FIG. 14A showing initiation of energy delivery;

FIG. 18B corresponding to the view of FIG. 14B showing the propagation of the wavefronts of energy density outwardly; and FIG. 18C corresponding to the view of FIG. 14C showing the further outward propagation of the wavefronts of energy density to thereby weld tissue.

DETAILED DESCRIPTION OF THE INVENTION

Figure 3A:
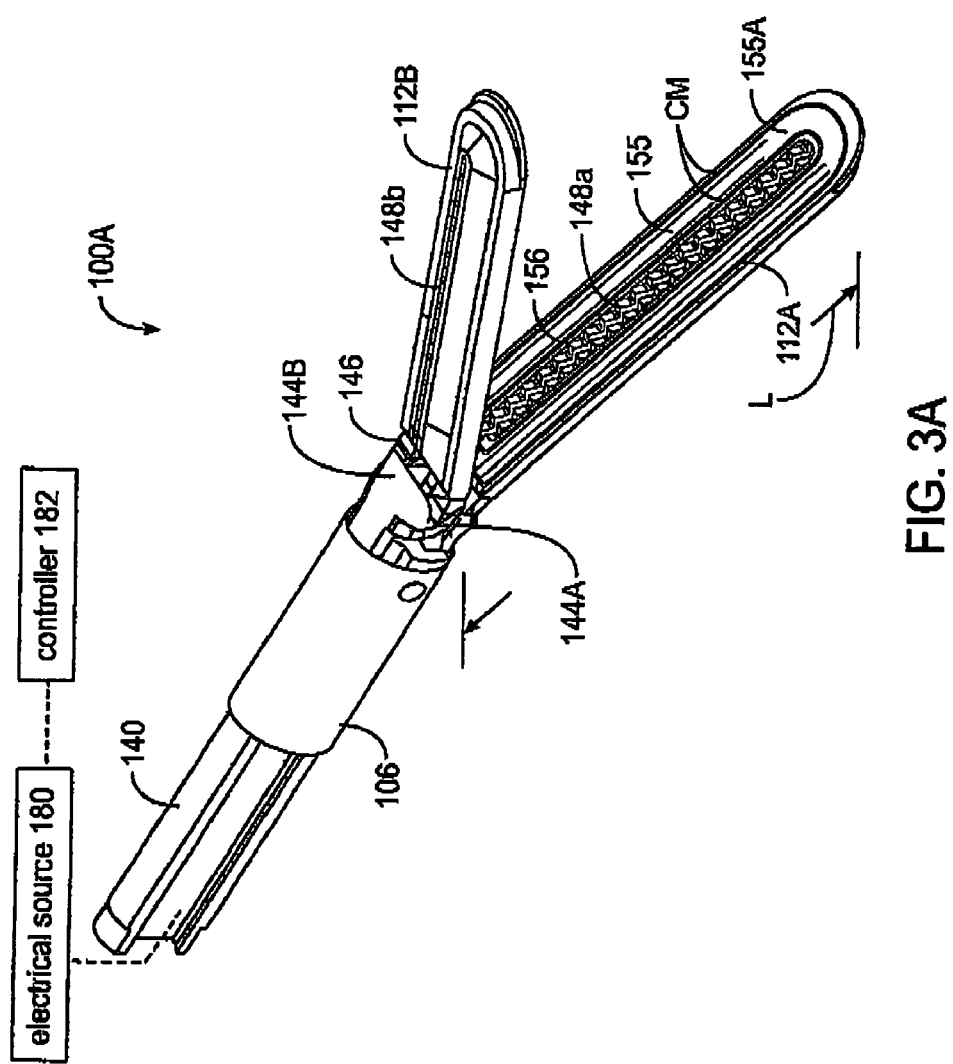
FIG. 3A is a perspective view of a jaw structure of tissue-transecting and welding instrument that carries a Type "A" conductive-resistive matrix system corresponding to the invention.
Figure 3B:
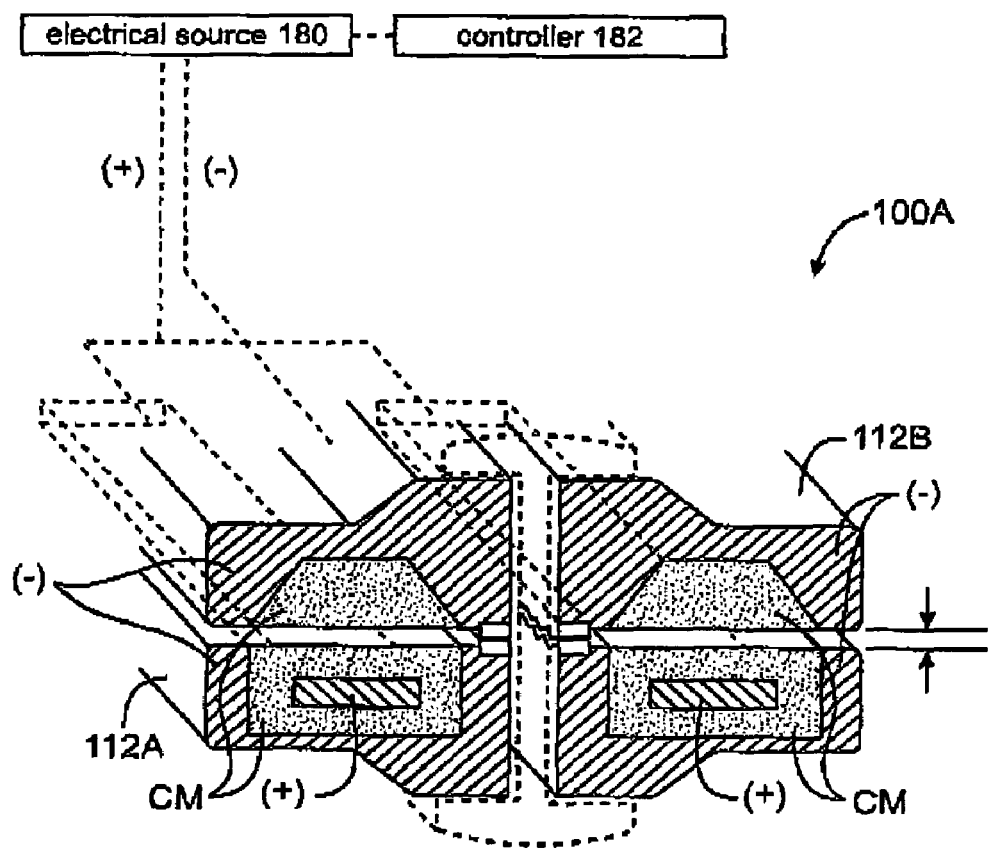
FIG. 3B is a sectional view of the jaw structure of FIG. 3A taken along line 3B—3B of FIG. 3A showing the location of conductive-resistive matrices.

1. Exemplary jaw structures for welding tissue. FIGS. 3A and 3B illustrate a working end of a surgical grasping instrument corresponding to the invention that is adapted for transecting captured tissue and for contemporaneously welding the captured tissue margins with controlled application of Rf energy. The jaw assembly 100A is carried at the distal end 104 of an introducer sleeve member 106 that can have a diameter ranging from about 2 mm. to 20 mm. for cooperating with cannulae in endoscopic surgeries or for use in open surgical procedures. The introducer portion 106 extends from a proximal handle (not shown). The handle can be any type of pistol-grip or other type of handle known in the art that carries actuator levers, triggers or sliders for actuating the jaws and need not be described in further detail. The introducer sleeve portion 106 has a bore 108 extending therethrough for carrying actuator mechanisms for actuating the jaws and for carrying electrical leads 109a–109b for delivery of electrical energy to electrosurgical components of the working end.

As can be seen in FIGS. 3A and 3B, the jaw assembly 100A has first (lower) jaw element 112A and second (upper) jaw element 112B that are adapted to close or approximate about axis 115. The jaw elements can both be moveable or a single jaw can rotate to provide the jaw-open and jaw-closed positions. In the exemplary embodiment of FIGS. 3A and 3B, both jaws are moveable relative to the introducer portion 106.

Of particular interest, the opening-closing mechanism of the jaw assembly 100A is capable of applying very high compressive forces on tissue on the basis of cam mechanisms with a reciprocating member 140. The engagement surfaces further provide a positive engagement of camming surfaces (i) for moving the jaw assembly to the (second) closed position to apply very high compressive forces, and (ii) for moving the jaws toward the (first) open position to apply substantially high opening forces for "dissecting" tissue. This important feature allows the surgeon to insert the tip of the closed jaws into a dissectable tissue plane—and thereafter open the jaws to apply such dissecting forces against tissues. Prior art instruments are spring-loaded toward the open position which is not useful for dissecting tissue.

In the embodiment of FIGS. 3A and 3B, a reciprocating member 140 is actuatable from the handle of the instrument by any suitable mechanism, such as a lever arm, that is coupled to a proximal end 141 of member 140. The proximal end 141 and medial portion of member 140 are dimensioned to reciprocate within bore 108 of introducer sleeve 106. The distal portion 142 of reciprocating member 140 carries first (lower) and second (upper) laterally-extending flange elements 144A and 144B that are coupled by an intermediate transverse element 145. The transverse element further is adapted to transect tissue captured between the jaws with a leading edge 146 (FIG. 3A) that can be a blade or a cutting electrode. The transverse element 145 is adapted to slide within a channels 148a and 148b in the paired first and second jaws to thereby open and close the jaws. The camming action of the reciprocating member 140 and jaw surfaces is described in complete detail in co-pending Provisional U.S. patent application Ser. No. 60/347,382 filed Jan. 11, 2002 titled Jaw Structure for Electrosurgical Instrument and Method of Use, which is incorporated herein by reference.

In FIGS. 3A and 3B, the first and second jaws 112A and 112B close about an engagement plane 150 and define tissue-engaging surface layers 155A and 155B that contact and deliver energy to engaged tissues from electrical energy means as will be described below. The jaws can have any suitable length with teeth or serrations 156 for gripping tissue. One preferred embodiment of FIGS. 3A and 3B provides such serrations 156 at an inner portion of the jaws along channels 148a and 148b thus allowing for substantially smooth engagement surface layers 155A and 155B laterally outward of the tissue-gripping elements. The axial length of jaws 112A and 112B indicated at L can be any suitable length depending on the anatomic structure targeted for transection and sealing and typically will range from about 10 mm. to 50 mm. The jaw assembly can apply very high compression over much longer lengths, for example up to about 200 mm., for resecting and sealing organs such as a lung or liver. The scope of the invention also covers jaw assemblies for an instrument used in micro-surgeries wherein the jaw length can be about 5.0 mm or less.

In the exemplary embodiment of FIGS. 3A and 3B, the engagement surface 155A of the lower jaw 112A is adapted to deliver energy to tissue, at least in part, through a conductive-resistive matrix CM corresponding to the invention. The tissue-contacting surface 155B of upper jaw 112B preferably carries a similar conductive-resistive matrix, or the surface can be a conductive electrode or and insulative layer as will be described below. Alternatively, the engagement surfaces of the jaws can carry any of the energy delivery components disclosed in co-pending U.S. patent application Ser. No. 10/032,867 filed Oct. 22, 2001 titled Electrosurgical Jaw Structure for Controlled Energy Delivery and U.S. patent application Ser. No. 10/308,362 filed Dec. 3, 2002 titled Electrosurgical Jaw Structure for Controlled Energy Delivery, both of which are incorporated herein by reference.

Figure 4:
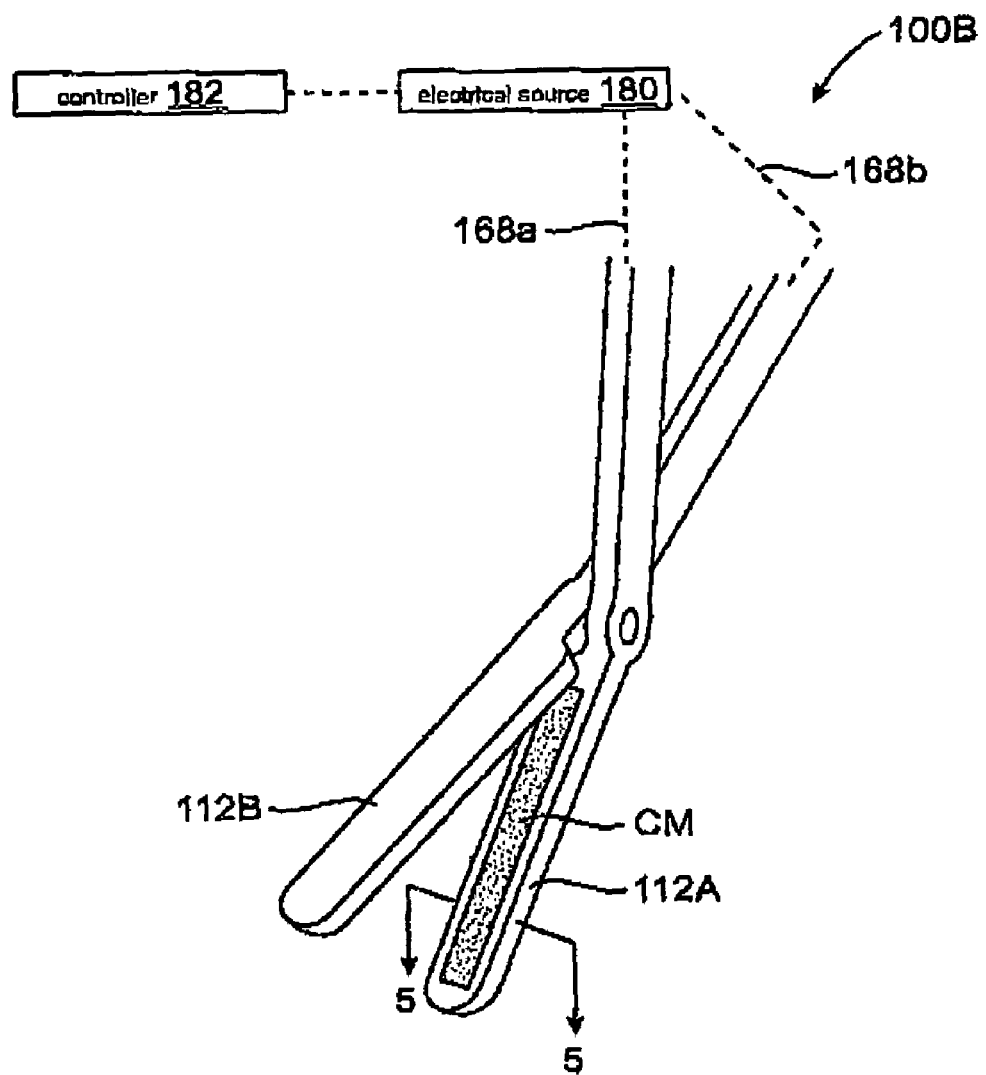
FIG. 4 is a perspective view of another exemplary surgical instrument that carries a Type "A" conductive-resistive matrix system for welding tissue.

Referring now to FIG. 4, an alternative jaw structure 100B is shown with lower and upper jaws having similar reference numerals 112A–112B. The simple scissor-action of the jaws in FIG. 4 has been found to be useful for welding tissues in procedures that do not require tissue transection. The scissor-action of the jaws can apply high compressive forces against tissue captured between the jaws to perform the method corresponding to the invention. As can be seen by comparing FIGS. 3B and 4, the jaws of either embodiment 100A or 100B can carry the same energy delivery components, which is described next.

It has been found that very high compression of tissue combined with controlled Rf energy delivery is optimal for welding the engaged tissue volume contemporaneous with transection of the tissue. Preferably, the engagement gap g between the engagement planes ranges from about 0.0005" to about 0.050" for reduce the engaged tissue to the thickness of a membrane. More preferably, the gap g between the engagement planes ranges from about 0.001" to about 0.005".

Figure 5:
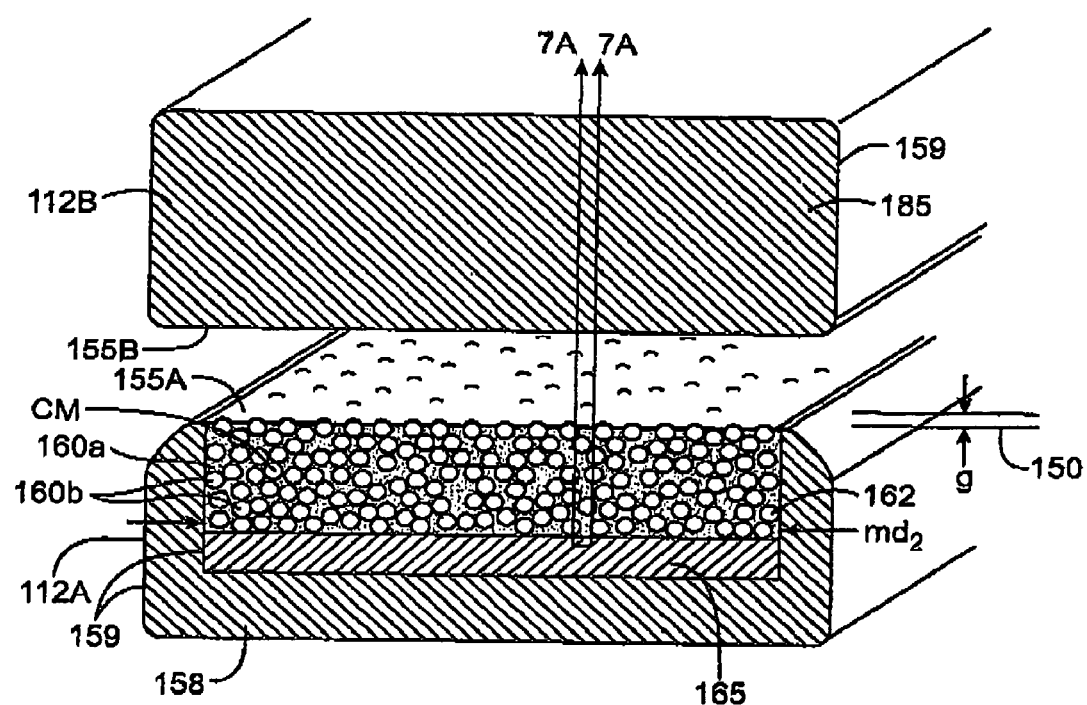
FIG. 5 is a sectional view of the jaw structure of FIG. 4 taken along line 5—5 of FIG. 4 showing details of the conductive-resistive matrix.

2. Type "A" conductive-resistive matrix system for controlled energy delivery in tissue welding. FIG. 5 illustrates an enlarged schematic sectional view of a jaw structure that carries engagement surface layers 155A and 155B in jaws 112A and 112B. It should be appreciated that the engagement surface layers 155A and 155B are shown in a scissors-type jaw (cf. FIG. 4) for convenience, and the conductive-resistive matrix system would be identical in each side of a transecting jaw structure as shown in FIGS. 3A–3B.

In FIG. 5, it can be seen that the lower jaw 112A carries a component described herein as a conductive-resistive matrix CM that is at least partly exposed to an engagement plane 150 that is defined as the interface between tissue and a jaw engagement surface layer, 155A or 155B. More in particular, the conductive-resistive matrix CM comprises a first portion 160a and a second portion 160b. The first portion is preferably an electrically nonconductive material that has a selected coefficient of expansion that is typically greater than the coefficient of expansion of the material of the second portion. In one preferred embodiment, the first portion 160a of the matrix is an elastomer, for example a medical grade silicone. The first portion 160a of the matrix also is preferably not a good thermal conductor. Other thermoplastic elastomers fall within the scope of the invention, as do ceramics having a thermal coefficient of expansion with the parameters further described below.

Referring to FIG. 5, the second portion 160b of the matrix CM is a material that is electrically conductive and that is distributed within the first portion 160a. In FIG. 5, the second portion 160b is represented (not-to-scale) as spherical elements 162 that are intermixed within the elastomer first portion 160a of matrix CM. The elements 162 can have any regular or irregular shape, and also can be elongated elements or can comprise conductive filaments. The dimensions of elements 162 can range from nanoparticles having a scale of about 1 nm. to 2 nm. across a principal axis thereof to much larger cross-sections of about 100 microns in a typical jaw structure. In a very large jaw, the elements 162 in matrix CM can have a greater dimension that 100 microns in a generally spherical form. Also, the matrix CM can carry a second portion 160b in the form of an intertwined filament (or filaments) akin to the form of steel wool embedded within an elastomeric first portion 160a and fall within the scope the invention. Thus, the second portion 160b can be of any form that distributes an electrically conductive mass within the overall volume of the matrix CM.

In the lower jaw 112A of FIG. 5, the matrix CM is carried in a support structure or body portion 158 that can be of any suitable metal or other material having sufficient strength to apply high compressive forces to the engaged tissue. Typically, the support structure 158 carries an insulative coating 159 to prevent electrical current flow to tissues about the exterior of the jaw assembly and between support structure 158 and the matrix CM and a conductive element 165 therein.

Of particular interest, the combination of first and second portions 160a and 160b provide a matrix CM that is variably resistive (in ohms-centimeters) in response to temperature changes therein. The matrix composition with the temperature-dependent resistance is alternatively described herein as a temperature coefficient material. In one embodiment, by selecting the volume proportion of first portion 160a of the non-conductive elastomer relative to the volume proportion of second portion 160b of the conductive nanoparticles or elements 162, the matrix CM can be engineered to exhibit very large changes in resistance with a small change in matrix temperature. In other words, the change of resistance with a change in temperature results in a "positive" temperature coefficient of resistance.

Figure 6:
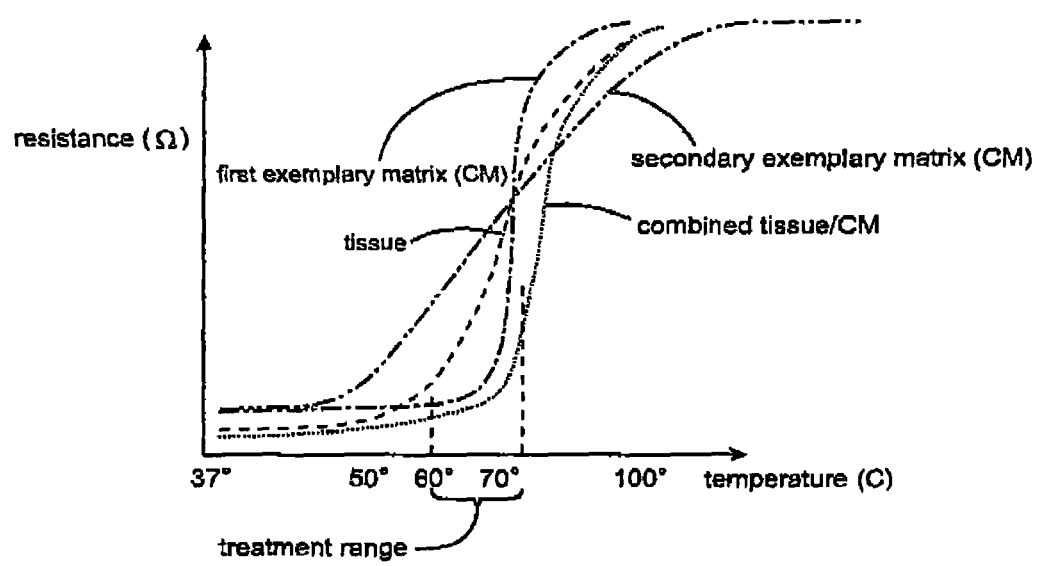
FIG. 6 is a graph showing (i) temperature-resistance profiles of alternative conductive-resistive matrices that can be carried in the jaw of FIG. 5, (ii) the impedance of tissue, and (iii) the combined resistance of the matrix and tissue as measured by a system controller.

In a first preferred embodiment, the matrix CM is engineered to exhibit unique resistance vs. temperature characteristics that is represented by a positively sloped temperature-resistance curve (see FIG. 6). More in particular, the first exemplary matrix CM indicated in FIG. 6 maintains a low base resistance over a selected base temperature range with a dramatically increasing resistance above a selected narrow temperature range of the material (sometimes referred to herein as a switching range, see FIG. 6). For example, the base resistance can be low, or the electrical conductivity high, between about 37° C. and 65° C., with the resistance increasing greatly between about 65° C. and 75° C. to substantially limit conduction therethrough (at typically utilized power levels in electrosurgery). In a second exemplary matrix embodiment described in FIG. 6, the matrix CM is characterized by a more continuously positively sloped temperature-resistance over the range of 50° C. to about 80° C. Thus, the scope of the invention includes any specially engineered matrix CM with such a positive slope that is suitable for welding tissue as described below.

In one preferred embodiment, the matrix CM has a first portion 160a fabricated from a medical grade silicone that is doped with a selected volume of conductive particles, for example carbon particles in sub-micron dimensions as described above. By weight, the ration of silicone-to-carbon can range from about 10/90 to about 70/30 (silicone/carbon) to provide the selected range at which the inventive composition functions to substantially limit electrical conductance therethrough. More preferably, the carbon percentage in the matrix CM is from about 40% to 80% with the balance being silicone. In fabricating a matrix CM in this manner, it is preferable to use a carbon type that has single molecular bonds. It is less preferable to use a carbon type with double bonds that has the potential of breaking down when used in a small cross-section matrix, thus creating the potential of a permanent conductive path within deteriorated particles of the matrix CM that fuse together. One preferred composition has been developed to provide a thermal treatment range of about 75° C. to 80° C. with the matrix having about 50–60 percent carbon the balance being silicone. The matrix CM corresponding to the invention thus becomes reversibly resistant to electric current flow at the selected higher temperature range, and returns to be substantially conductive within the base temperature range. In one preferred embodiment, the hardness of the silicone-based matrix CM is within the range of about Shore A range of less than about 95. More preferably, an exemplary silicone-based matrix CM has Shore A range of from about 20–80. The preferred hardness of the silicone-based matrix CM is about 150 or lower in the Shore D scale. As will be described below, some embodiments have jaws that carry cooperating matrix portions having at least two different hardness ratings.

In another embodiment, the particles or elements 162 can be a polymer bead with a thin conductive coating. A metallic coating can be deposited by electroless plating processes or other vapor deposition process known in the art, and the coating can comprise any suitable thin-film deposition, such as gold, platinum, silver, palladium, tin, titanium, tantalum, copper or combinations or alloys of such metals, or varied layers of such materials. One preferred manner of depositing a metallic coating on such polymer elements comprises an electroless plating process provided by Micro Plating, Inc., 8110 Hawthorne Dr., Erie, Pa. 16509-4654. The thickness of the metallic coating can range from about 0.00001" to 0.005". (A suitable conductive-resistive matrix CM can comprise a ceramic first portion 160a in combination with compressible-particle second portion 160b of a such a metallized polymer bead to create the effects illustrated in FIGS. 8A–8B below).

One aspect of the invention relates to the use of a matrix CM as illustrated schematically in FIG. 5 in a jaw's engagement surface layer 155A with a selected treatment range between a first temperature ($TE_1$) and a second temperature ($TE_2$) that approximates the targeted tissue temperature for tissue welding (see FIG. 6). The selected switching range of the matrix as defined above, for example, can be any substantially narrow 1°–10° C. range that is about the maximum of the treatment range that is optimal for tissue welding. For another thermotherpy, the switching range can fall within any larger tissue treatment range of about 50°–200° C.

No matter the character of the slope of the temperature-resistance curve of the matrix CM (see FIG. 6), a preferred embodiment has a matrix CM that is engineered to have a selected resistance to current flow across its selected dimensions in the jaw assembly, when at 37° C. that ranges from about 0.0001 ohms to 1000 ohms. More preferably, the matrix CM has a designed resistance across its selected dimensions at 37° C. that ranges from about 1.0 ohm to 1000 ohms. Still more preferably, the matrix CM has with a designed resistance across its selected dimensions at 37° C. that ranges from about 25 ohms to 150 ohms. In any event, the selected resistance across the matrix CM in an exemplary jaw at 37° C. matches or slightly exceeds the resistance of the tissue or body structure that is engaged. The matrix CM further is engineered to have a selected conductance that substantially limits current flow thererough corresponding to a selected temperature that constitutes the high end (maximum) of the targeted thermal treatment range. As generally described above, such a maximum temperature for tissue welding can be a selected temperature between about 50° C. and 90° C. More preferably, the selected temperature at which the matrix's selected conductance substantially limits current flow occurs at between about 60° C. and 80° C.

In the exemplary jaw 112A of FIG. 5, the entire surface area of engagement surface layer 155A comprises the conductive-resistive matrix CM, wherein the engagement surface is defined as the tissue-contacting portion that can apply electrical potential to tissue. Preferably, any instrument's engagement surface has a matrix CM that comprises at least 5% of its surface area. More preferably, the matrix CM comprises at least 10% of the surface area of engagement surface. Still more preferably, the matrix CM comprises at least 20% of the surface area of the jaw's engagement surface. The matrix CM can have any suitable cross-sectional dimensions, indicated generally at $md_1$ and $md_2$ in FIG. 5, and preferably such a cross-section comprises a significant fractional volume of the jaw relative to support structure 158. As will be described below, in some embodiments, it is desirable to provide a thermal mass for optimizing passive conduction of heat to engaged tissue.

As can be seen in FIG. 5, the interior of jaw 112A carries a conductive element (or electrode) indicated at 165 that interfaces with an interior surface 166 of the matrix CM. The conductive element 165 is coupled by an electrical lead 109a to a voltage (Rf) source 180 and optional controller 182 (FIG. 4). Thus, the Rf source 180 can apply electrical potential (of a first polarity) to the matrix CM through conductor 165—and thereafter to the engagement plane 150 through matrix CM. The opposing second jaw 112B in FIG. 5 has a conductive material (electrode) indicated at 185 coupled to source 180 by lead 109b that is exposed within the upper engagement surface 155B.

In a first mode of operation, referring to FIG. 5, electrical potential of a first polarity applied to conductor 165 will result in current flow through the matrix CM and the engaged tissue et to the opposing polarity conductor 185. As described previously, the resistance of the matrix CM at 37° C. is engineered to approximate, or slightly exceed, that of the engaged tissue et. It can now be described how the engagement surface 155A can modulate the delivery of energy to tissue et similar to the hypothetical engagement surface of FIG. 2. Consider that the small sections of engagement surfaces represent the micron-sized, surface areas (or pixels) of the illustration of FIG. 2 (note that the jaws are not in a fully closed position in FIG. 5). The preferred membrane-thick engagement gap g is graphically represented in FIG. 5.

Figure 7A:
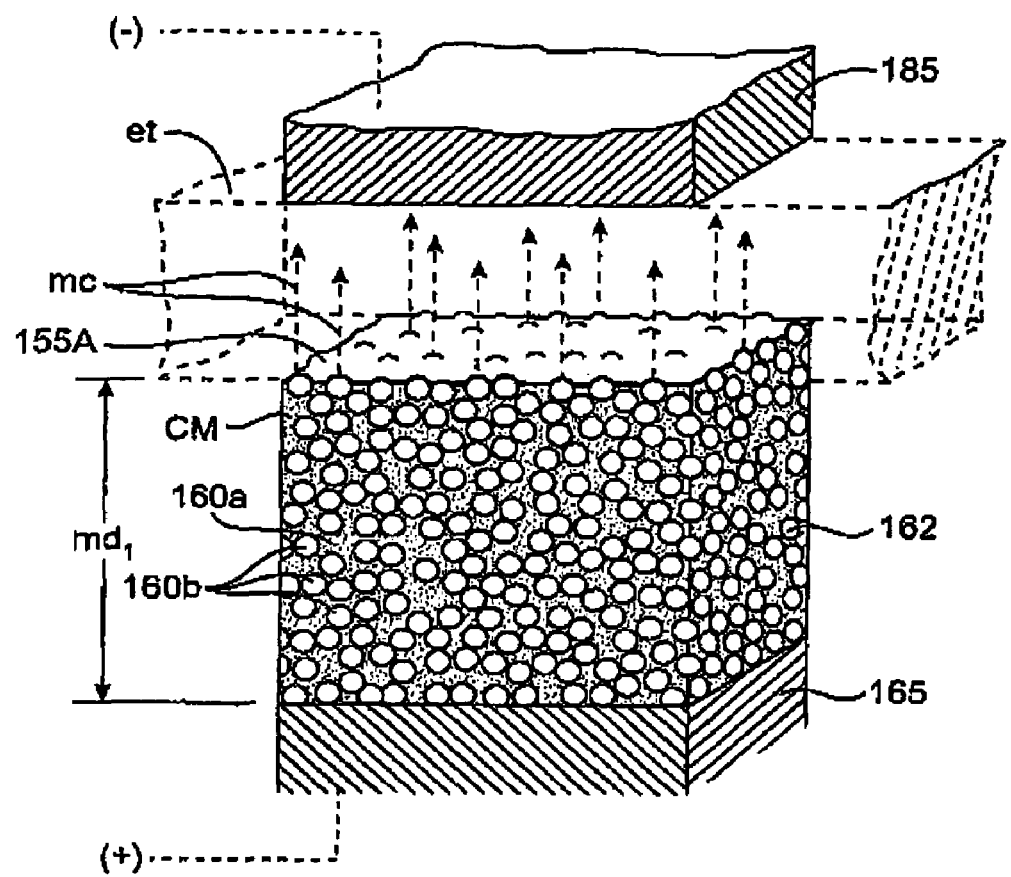
FIG. 7A is an enlarged view of a portion of the conductive-resistive matrix and jaw body of FIG. 5 showing a first portion of an elastomer and a second portion of conductive particles at a resting temperature.
Figure 8A:
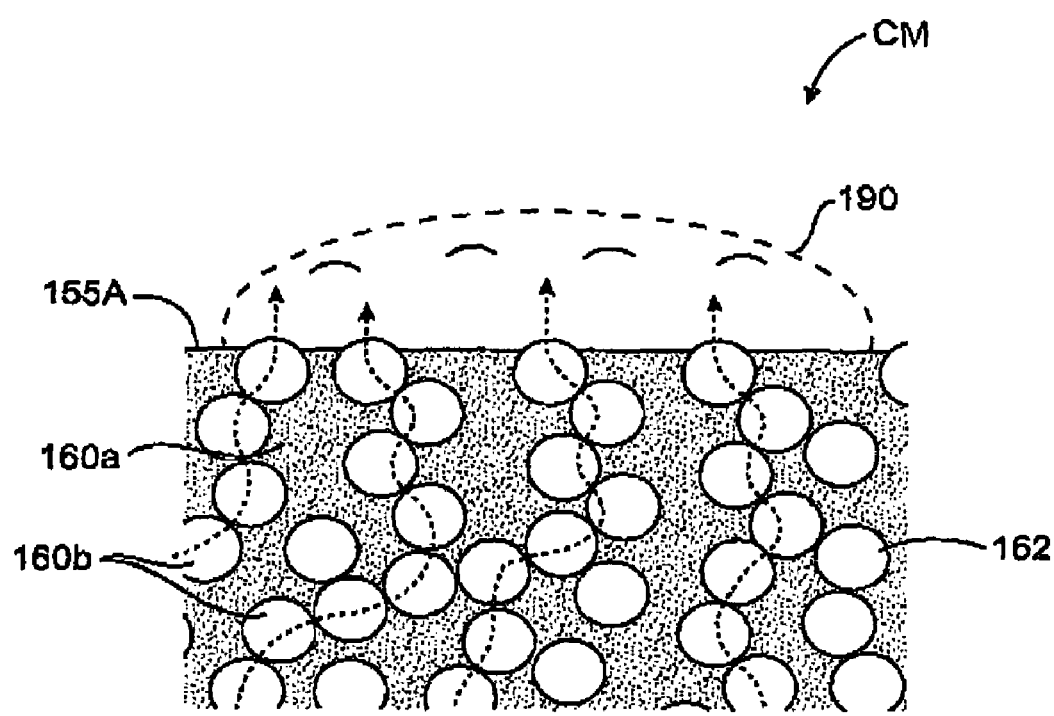
FIG. 8A is a further enlarged view of the conductive-resistive matrix of FIG. 7A showing the first portion (elastomer) and the second portion (conductive elements) and paths of microcurrents therethrough.

FIGS. 7A and 8A illustrate enlarged schematic sectional views of jaws 112A and 112B and the matrix CM. It can be understood that the electrical potential at conductor 165 will cause current flow within and about the elements 162 of second portion 160b along any conductive path toward the opposing polarity conductor 185. FIG. 8A more particularly shows a graphic representation of paths of microcurrents $mc_m$ within the matrix wherein the conductive elements 162 are in substantial contact. FIG. 7A also graphically illustrates paths of microcurrents $mc_t$ in the engaged tissue across gap g. The current paths in the tissue (across conductive sodium, potassium, chlorine ions etc.) thus results in ohmic heating of the tissue engaged between jaws 112A and 112B. In fact, the flux of microcurrents $mc_m$ within the matrix and the microcurrents $mc_t$ within the engaged tissue will seek the most conductive paths—which will be assisted by the positioning of elements 162 in the surface of the engagement layer 155A, which can act like surface asperities or sharp edges to induce current flow therefrom.

Figure 7B:
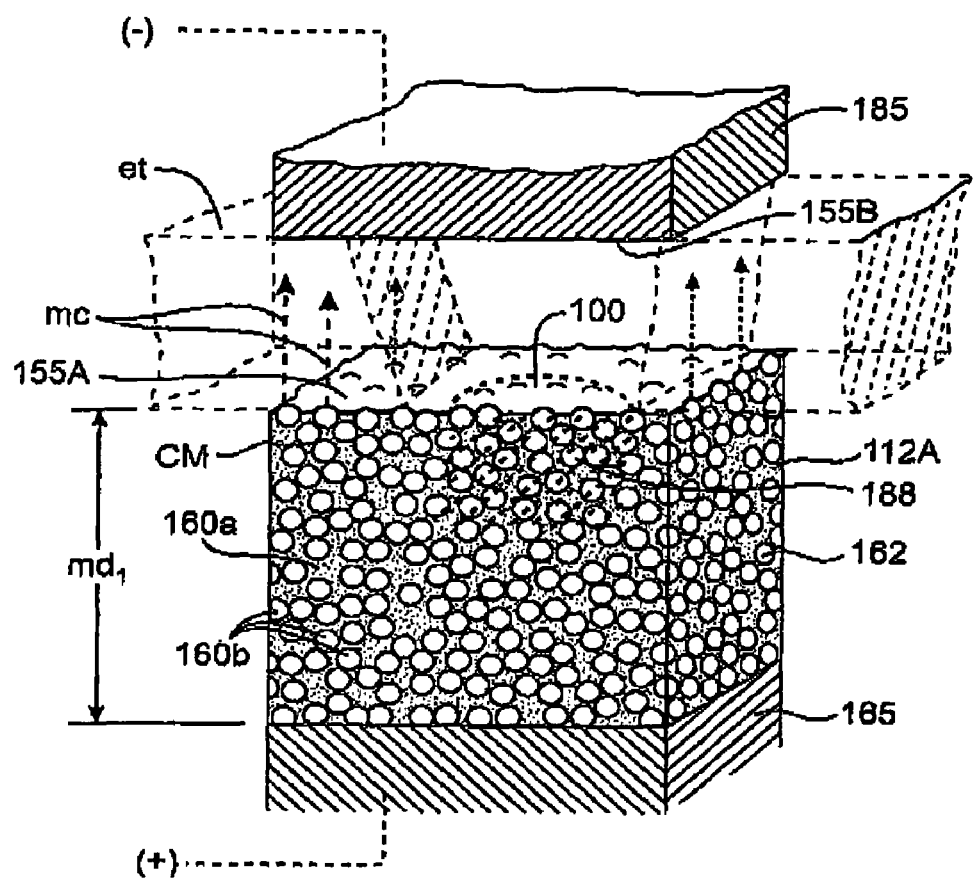
FIG. 7B is another view the conductive-resistive matrix and jaw body of FIG. 7A after a portion is elevated to a higher temperature to modulate microcurrent flow therethrough thus depicting a method of the invention in spatially localizing and modulating Rf energy application from a conductive-resistive matrix that engages tissue.
Figure 8B:
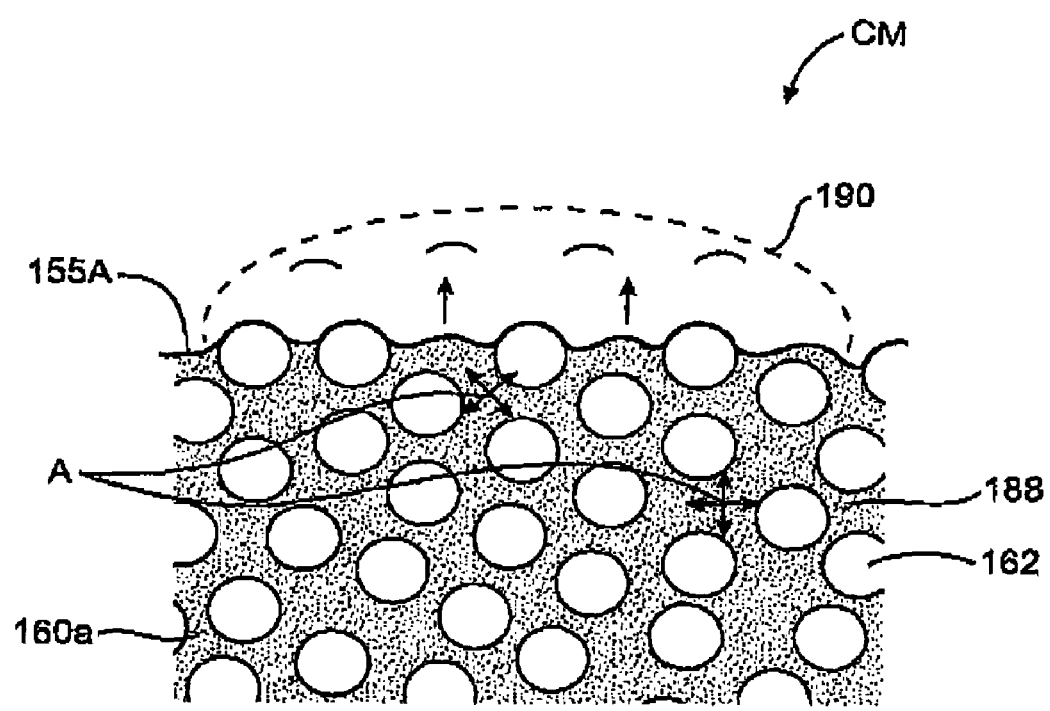
FIG. 8B is a further enlarged view of matrix of FIG. 7B showing the effect of increased temperature and the manner in which resistance to microcurrent flow is caused in the method of spatially localizing and modulating Rf energy application.

Consider that ohmic heating (or active heating) of the shaded portion 188 of engaged tissue et in FIGS. 7B and 8B elevates its temperature to a selected temperature at the maximum of the targeted range. Heat will be conducted back to the matrix portion CM proximate to the heated tissue. At the selected temperature, the matrix CM will substantially reduce current flow therethrough and thus will contribute less and less to ohmic tissue heating, which is represented in FIGS. 7B and 8B. In FIGS. 7B and 8B, the thermal coefficient of expansion of the elastomer of first matrix portion 160a will cause slight redistribution of the second conductive portion 160b within the matrix—naturally resulting in lessened contacts between the conductive elements 162. It can be understood by arrows A in FIG. 8B that the elastomer will expand in directions of least resistance which is between the elements 162 since the elements are selected to be substantially resistant to compression.

Of particular interest, the small surface portion of matrix CM indicated at 190 in FIG. 8A will function, in effect, independently to modulate power delivery to the surface of the tissue T engaged thereby. This effect will occur across the entire engagement surface layer 155A, to provide practically infinite "spatially localized" modulation of active energy density in the engaged tissue. In effect, the engagement surface can be defined as having "pixels" about its surface that are independently controlled with respect to energy application to localized tissue in contact with each pixel. Due to the high mechanical compression applied by the jaws, the engaged membrane all can be elevated to the selected temperature contemporaneously as each pixel heats adjacent tissue to the top of treatment range. As also depicted in FIG. 8B, the thermal expansion of the elastomeric matrix surface also will push into the membrane, further insuring tissue contact along the engagement plane 150 to eliminate any possibility of an energy arc across a gap.

Of particular interest, as any portion of the conductive-resistive matrix CM falls below the upper end of targeted treatment range, that matrix portion will increase its conductance and add ohmic heating to the proximate tissue via current paths through the matrix from conductor 165. By this means of energy delivery, the mass of matrix and the jaw body will be modulated in temperature, similar to the engaged tissue, at or about the targeted treatment range.

Figure 9:
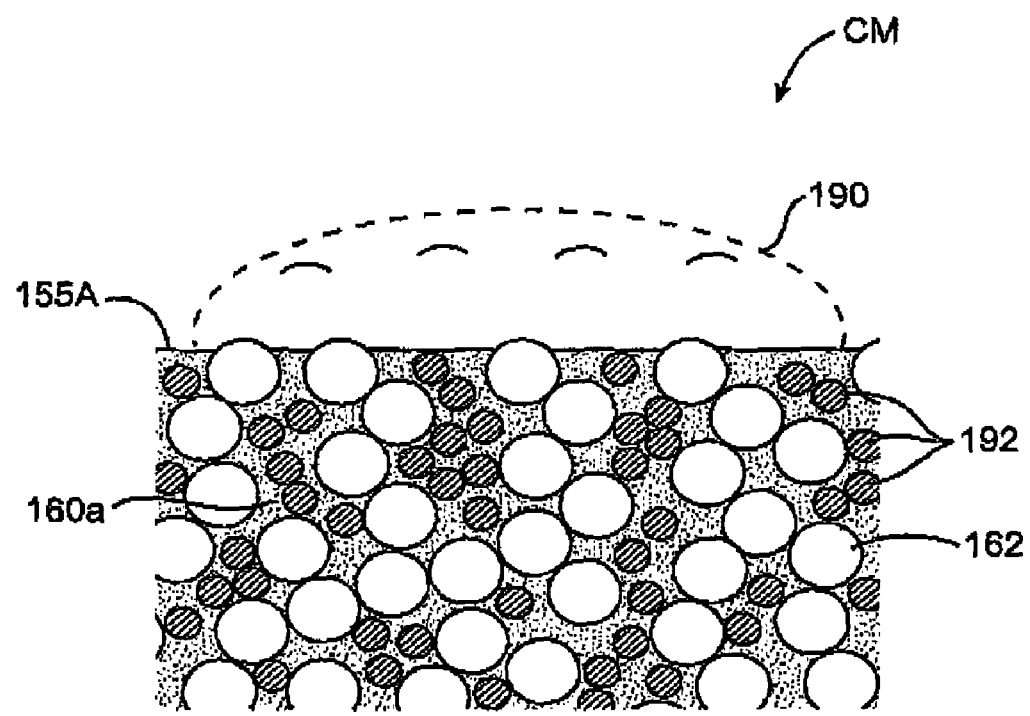
FIG. 9 is an enlarged view of an alternative conductive-resistive matrix similar to that of FIG. 7A that is additionally doped with thermally conductive, electrically non-conductive particles.

FIG. 9 shows another embodiment of a conductive-resistive matrix CM that is further doped with elements 192 of a material that is highly thermally conductive with a selected mass that is adapted to provide substantial heat capacity. By utilizing such elements 192 that may not be electrically conductive, the matrix can provide greater thermal mass and thereby increase passive conductive or convective heating of tissue when the matrix CM substantially reduces current flow to the engaged tissue. In another embodiment (not shown) the material of elements 162 can be both substantially electrically conductive and highly thermally conductive with a high heat capacity.

The manner of utilizing the system of FIGS. 7A–7B to perform the method of the invention can be understood as mechanically compressing the engaged tissue et to membrane thickness between the first and second engagement surfaces 155A and 155B of opposing jaws and thereafter applying electrical potential of a frequency and power level known in electrosurgery to conductor 165, which potential is conducted through matrix CM to maintain a selected temperature across engaged tissue et for a selected time interval. At normal tissue temperature, the low base resistance of the matrix CM allows unimpeded Rf current flow from voltage source 180 thereby making 100 percent of the engagement surface an active conductor of electrical energy. It can be understood that the engaged tissue initially will have a substantially uniform impedance to electrical current flow, which will increase substantially as the engaged tissue loses moisture due to ohmic heating. Following an arbitrary time interval (in the microsecond to ms range), the impedance of the engaged tissue—reduced to membrane thickness—will be elevated in temperature and conduct heat to the matrix CM. In turn, the matrix CM will constantly adjust microcurrent flow therethrough—with each square micron of surface area effectively delivering its own selected level of power depending on the spatially-local temperature. This automatic reduction of localized microcurrents in tissue thus prevents any dehydration of the engaged tissue. By maintaining the desired level of moisture in tissue proximate to the engagement plane(s), the jaw assembly can insure the effective denaturation of tissue constituents to thereafter create a strong weld.

Figure 1A:
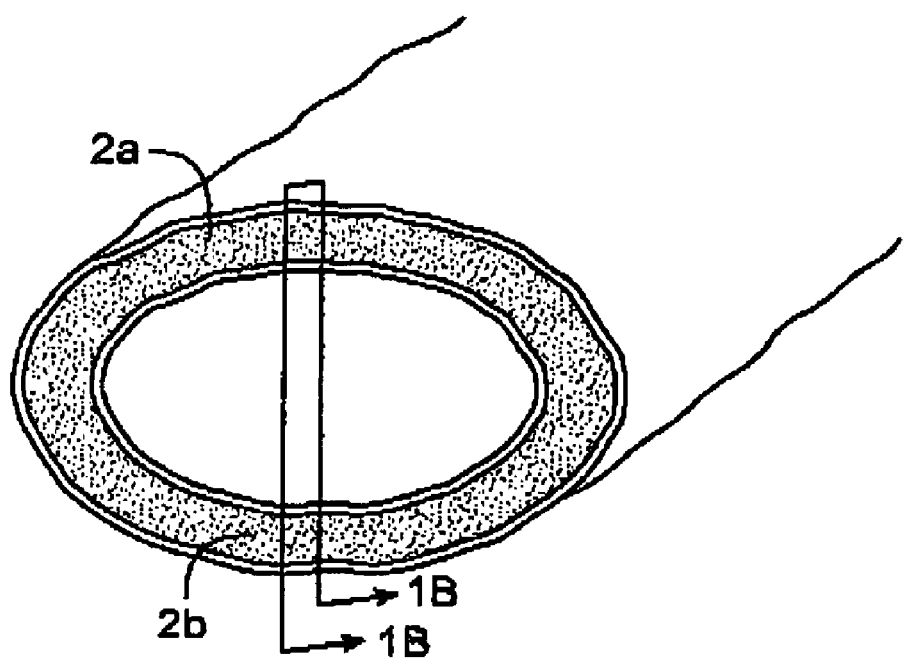
FIG. 1A is a view of a blood vessel targeted for welding.
Figure 1B:
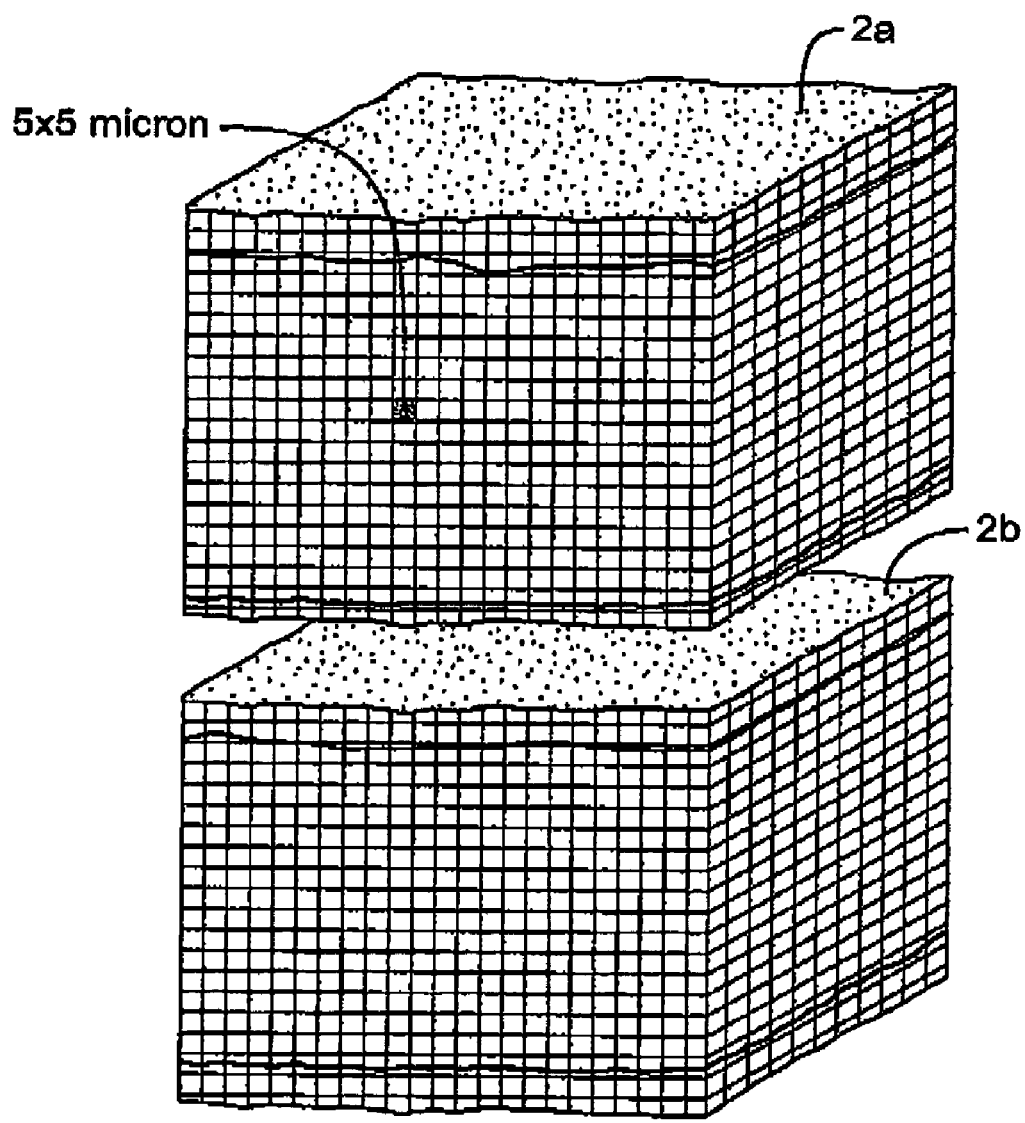
FIG. 1B is a greatly enlarged sectional view of opposing wall portions of the blood vessel of FIG. 1A taken along line 1B—1B of FIG. 1A.
Figure 1C:
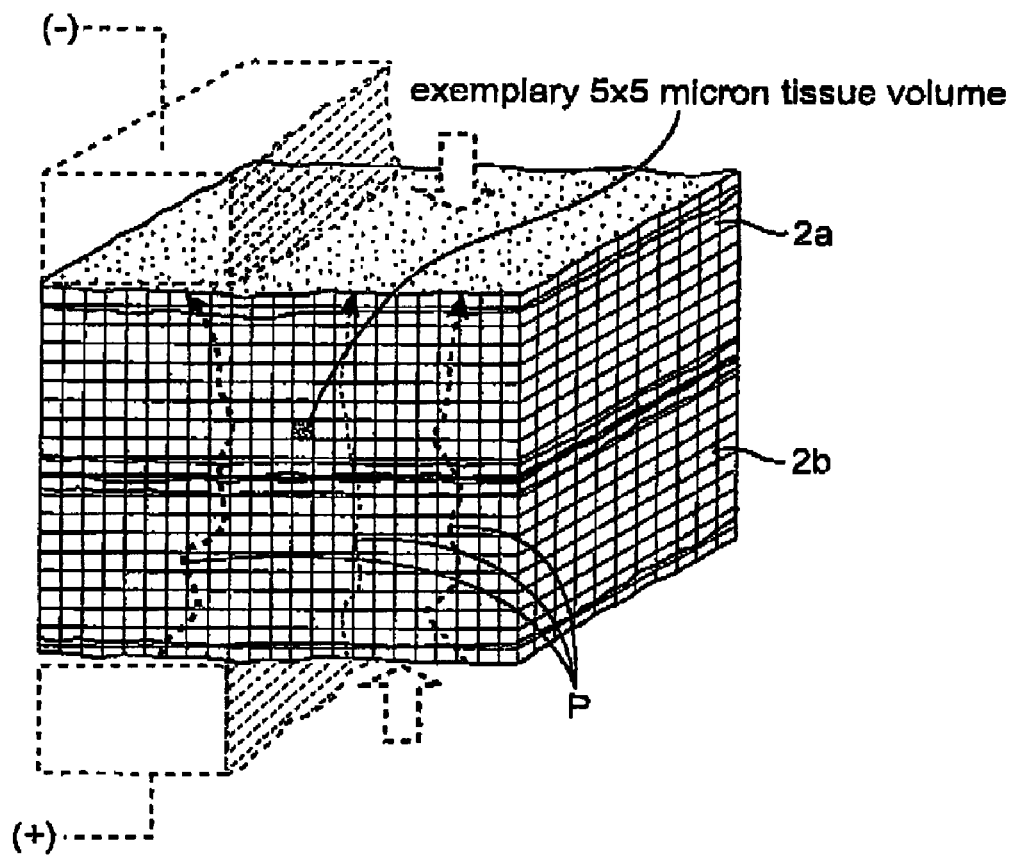
FIG. 1C is a graphic representation of opposing walls of a blood vessel engaged by prior art electrosurgical jaws showing random paths of current (causing ohmic heating) across the engaged tissue between opposing polarity electrodes.
Figure 1D:
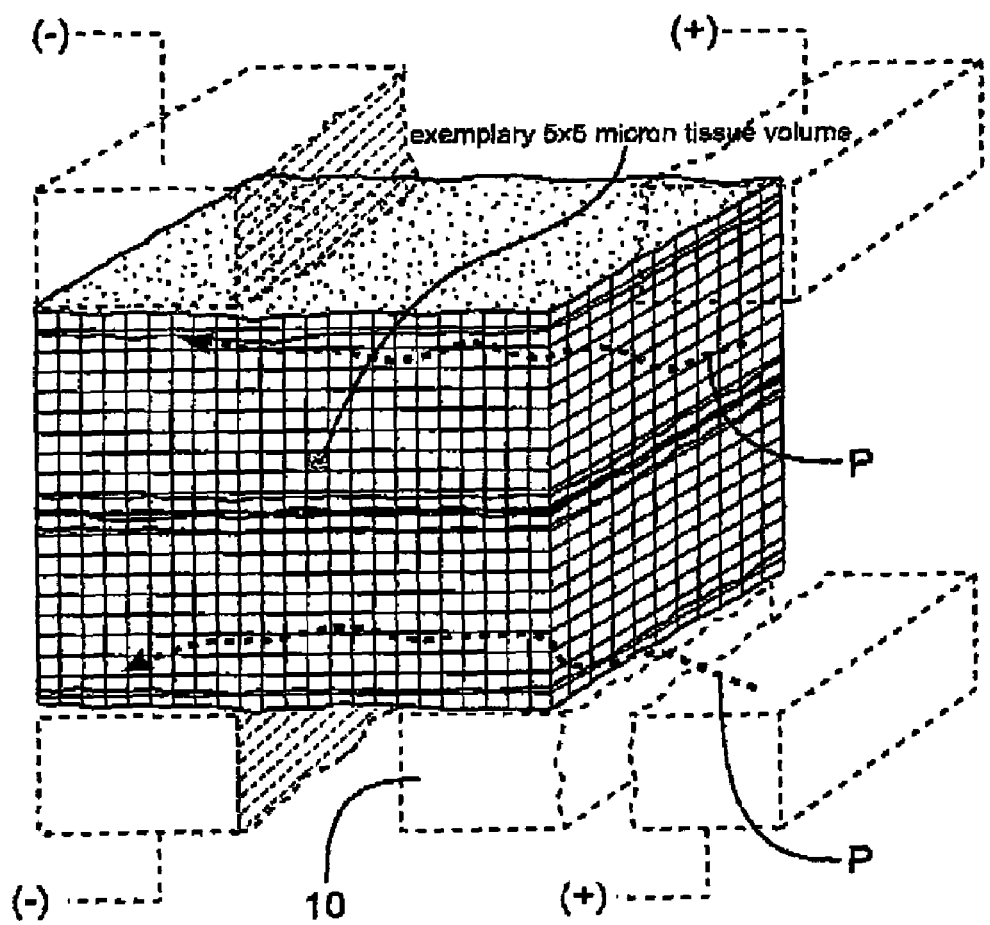
FIG. 1D is a graphic representation of a blood vessel engaged by prior art electrosurgical jaws with an insulator between opposing polarity electrodes on each side of the tissue showing random paths of current (ohmic heating).
Figure 2:
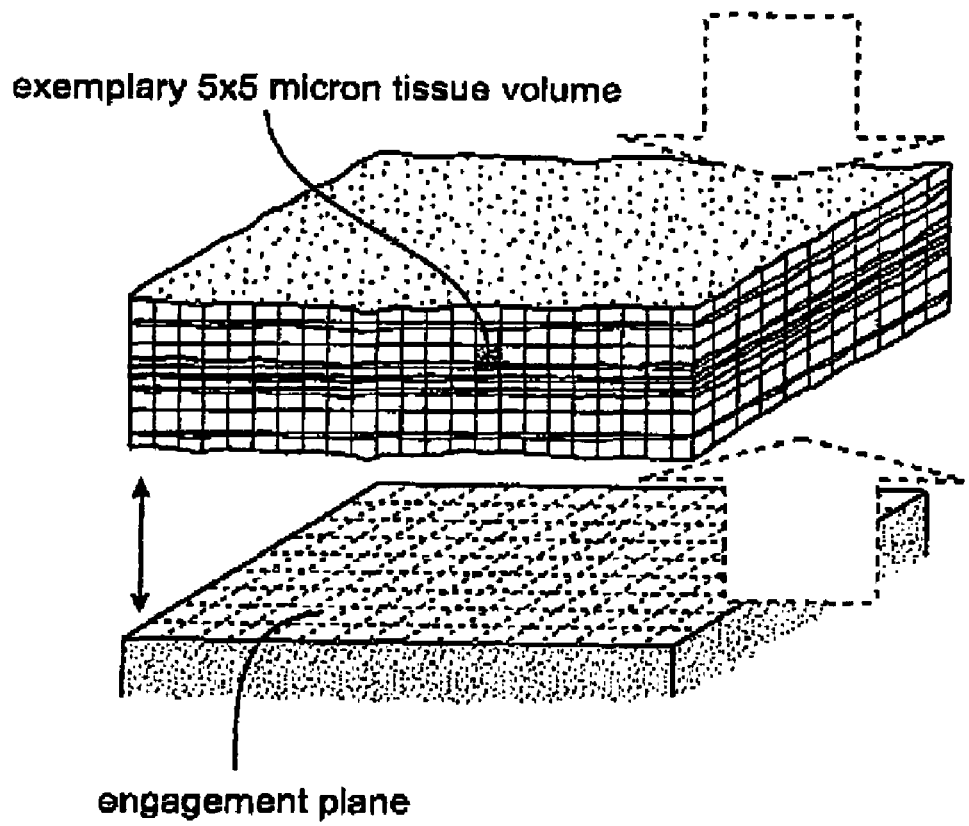
FIG. 2 graphically represents a blood vessel engaged by hypothetical electrosurgical jaws under very high compression with an energy-delivery surface proximate to the tissue.

By the above-described mechanisms of causing the matrix CM to be maintained in a selected treatment range, the actual Rf energy applied to the engaged tissue et can be precisely modulated, practically pixel-by-pixel, in the terminology used above to describe FIG. 2. Further, the elements 192 in the matrix CM can comprise a substantial volume of the jaws' bodies and the thermal mass of the jaws, so that when elevated in temperature, the jaws can deliver energy to the engaged tissue by means of passive conductive heating—at the same time Rf energy delivery in modulated as described above. This balance of active Rf heating and passive conductive heating (or radiative, convective heating) can maintain the targeted temperature for any selected time interval.

Of particular interest, the above-described method of the invention that allows for immediate modulation of ohmic heating across the entirety of the engaged membrane is to be contrasted with prior art instruments that rely on power modulation based on feedback from a temperature sensor. In systems that rely on sensors or thermocouples, power is modulated only to an electrode in its totality. Further, the prior art temperature measurements obtained with sensors is typically made at only at a single location in a jaw structure, which cannot be optimal for each micron of the engagement surface over the length of the jaws. Such temperature sensors also suffer from a time lag. Still further, such prior art temperature sensors provide only an indirect reading of actual tissue temperature—since a typical sensor can only measure the temperature of the electrode.

Other alternative modes of operating the conductive-resistive matrix system are possible. In one other mode of operation, the system controller 182 coupled to voltage source 180 can acquire data from current flow circuitry that is coupled to the first and second polarity conductors in the jaws (in any locations described previously) to measure the blended impedance of current flow between the first and second polarity conductors through the combination of (i) the engaged tissue and (ii) the matrix CM. This method of the invention can provide algorithms within the system controller 182 to modulate, or terminate, power delivery to the working end based on the level of the blended impedance as defined above. The method can further include controlling energy delivery by means of power-on and power-off intervals, with each such interval having a selected duration ranging from about 1 microsecond to one second. The working end and system controller 182 can further be provided with circuitry and working end components of the type disclosed in Provisional U.S. Patent Application Ser. No. 60/339,501 filed Nov. 9, 2001 titled Electrosurgical Instrument, which is incorporated herein by reference.

In another mode of operation, the system controller 182 can be provided with algorithms to derive the temperature of the matrix CM from measured impedance levels—which is possible since the matrix is engineered to have a selected unique resistance at each selected temperature over a temperature-resistance curve (see FIG. 6). Such temperature measurements can be utilized by the system controller 182 to modulate, or terminate, power delivery to engagement surfaces based on the temperature of the matrix CM. This method also can control energy delivery by means of the power-on and power-off intervals as described above.

Figure 10:
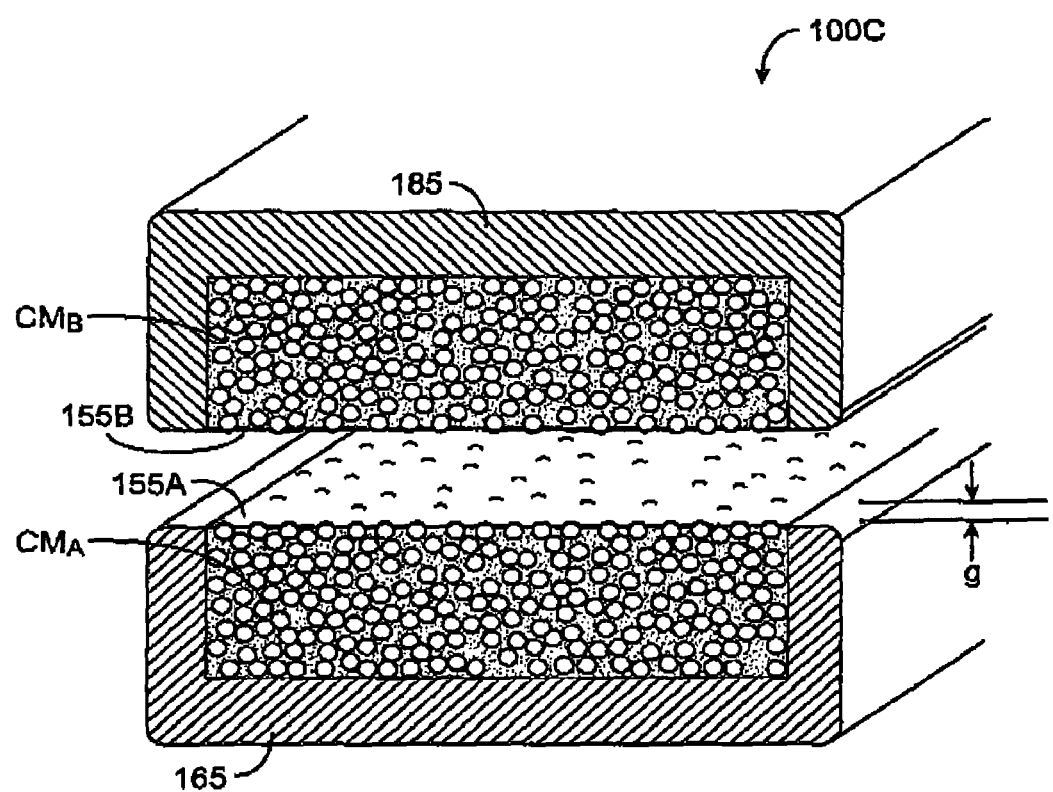
FIG. 10 is an alternative jaw structure similar to that of FIGS. 5 and 7A except carrying conductive-resistive matrices in the engagement surfaces of both opposing jaws.
Figure 11:
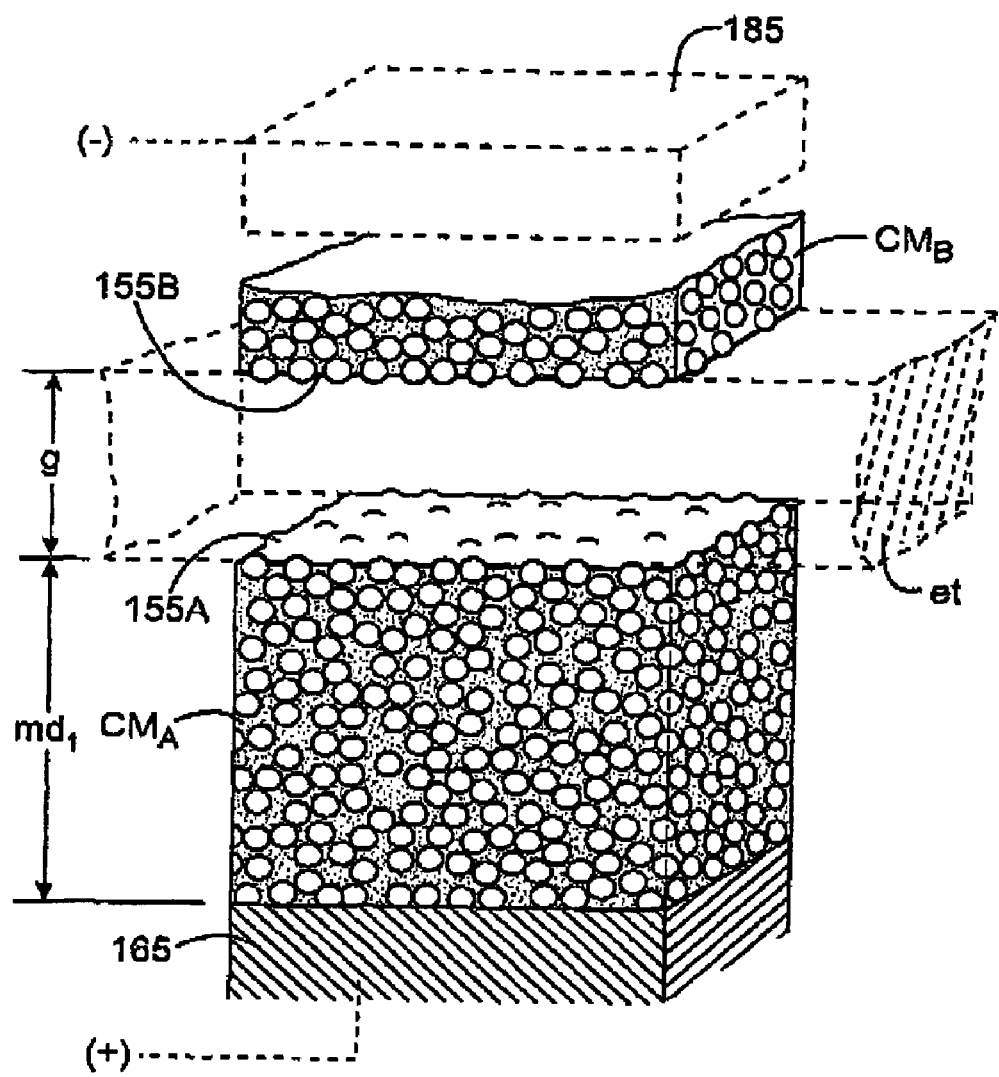
FIG. 11 is a greatly enlarged sectional view of the jaws of FIG. 10 taken along line 11—11 of FIG. 10.

FIGS. 10–11 illustrate a sectional views of an alternative jaw structure 100C—in which both the lower and upper engagement surfaces 155A and 155B carry a similar conductive-resistive matrices indicated at $CM_A$ and $CM_B$. It can be easily understood that both opposing engagement surfaces can function as described in FIGS. 7A–7B and 8A–8B to apply energy to engaged tissue. The jaw structure of FIGS. 10–11 illustrate that the tissue is engaged on opposing sides by a conductive-resistive matrix, with each matrix $CM_A$ and $CM_B$ in contact with an opposing polarity electrode indicated at 165 and 185, respectively. It has been found that providing cooperating first and second conductive-resistive matrices in opposing first and second engagement surfaces can enhance and control both active ohmic heating and the passive conduction of thermal effects to the engaged tissue.

3. Type "B" conductive-resistive matrix system for tissue welding. FIGS. 12 and 14A–14C illustrate an exemplary jaw assembly 200 that carries a Type "B" conductive-resistive matrix system for (i) controlling Rf energy density and microcurrent paths in engaged tissue, and (ii) for contemporaneously controlling passive conductive heating of the engaged tissue. The system again utilizes an elastomeric conductive-resistive matrix CM although substantially rigid conductive-resistive matrices of a ceramic positive-temperature coefficient material are also described and fall within the scope of the invention. The jaw assembly 200 is carried at the distal end of an introducer member, and can be a scissor-type structure (cf. FIG. 4) or a transecting-type jaw structure (cf. FIGS. 3A–3B). For convenience, the jaw assembly 200 is shown as a scissor-type instrument that allows for clarity of explanation.

The Type "A" system and method as described above in FIGS. 5 and 7A–7B allowed for effective pixel-by-pixel power modulation—wherein microscale spatial locations can be considered to apply an independent power level at a localized tissue contact. The Type "B" conductive-resistive matrix system described next not only allows for spatially localized power modulation, it additionally provides for the timing and dynamic localization of Rf energy density in engaged tissues—which can thus create a "wave" or "wash" of a controlled Rf energy density across the engaged tissue reduced to membrane thickness.

Figure 12:
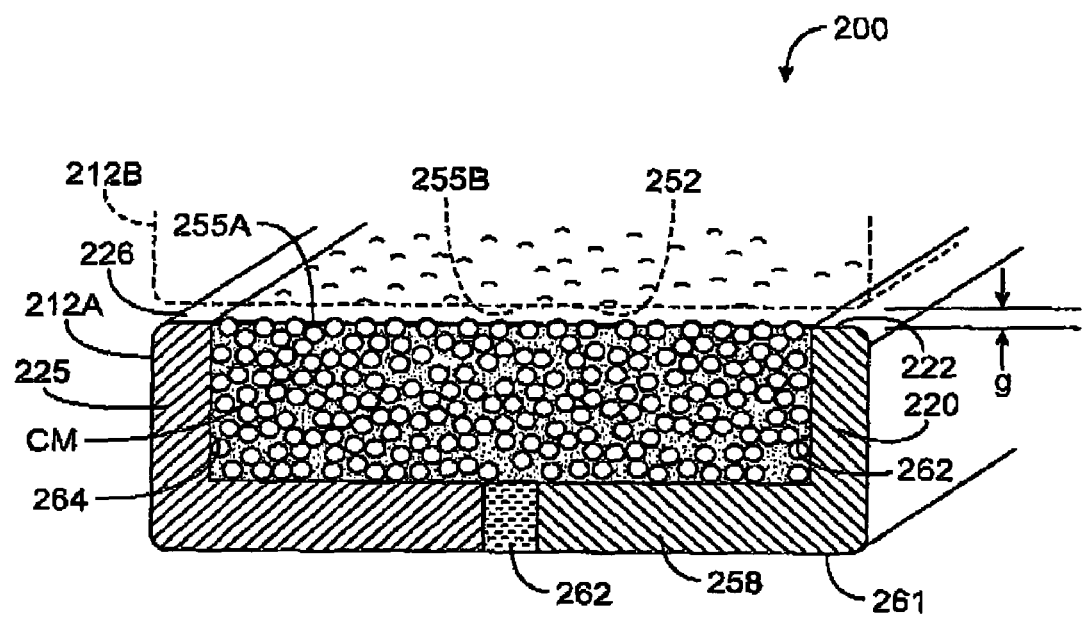
FIG. 12 is a sectional view of another exemplary jaw structure that carries a Type "B" conductive-resistive matrix system for welding tissue that utilizes opposing polarity electrodes with an intermediate conductive-resistive matrix in an engagement surface.

Of particular interest, referring to FIG. 12, the Type "B" system according to the invention provides an engagement surface layer of at least one jaw 212A and 212B with a conductive-resistive matrix CM intermediate a first polarity electrode 220 having exposed surface portion 222 and second polarity electrode 225 having exposed surface portion 226. Thus, the microcurrents within tissue during a brief interval of active heating can flow to and from said exposed surface portions 222 and 226 within the same engagement surface 255A. By providing opposing polarity electrodes 220 and 225 in an engagement surface with an intermediate conductive-resistive matrix CM, it has been found that the dynamic "wave" of energy density (ohmic heating) can be created that proves to be a very effective means for creating a uniform temperature in a selected cross-section of tissue to thus provide very uniform protein denaturation and uniform cross-linking on thermal relaxation to create a strong weld. While the opposing polarity electrodes 220 and 225 and matrix CM can he carried in both engagement surfaces 255A and 255B, the method of the invention can be more clearly described using the exemplary jaws of FIG. 11 wherein the upper jaw's engagement surface 250B is an insulator indicated at 252.

More in particular, referring to FIG. 12, the first (lower) jaw 212A is shown in sectional view with a conductive-resistive matrix CM exposed in a central portion of engagement surface 255A. A first polarity electrode 220 is located at one side of matrix CM with the second polarity electrode 225 exposed at the opposite side of the matrix CM. In the embodiment of FIG. 12, the body or support structure 258 of the jaw comprises the electrodes 220 and 225 with the electrodes separated by insulated body portion 262. Further, the exterior of the jaw body is covered by an insulator layer 261. The matrix CM is otherwise in contact with the interior portions 262 and 264 of electrodes 220 and 225, respectively.

Figure 13A:
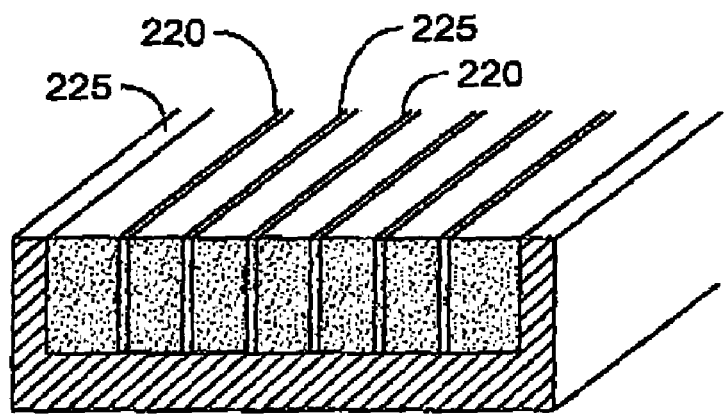
FIG. 13A is a sectional view of alternative Type "B" jaw with a plurality of opposing polarity electrodes with intermediate conductive-resistive matrices in the engagement surface.
Figure 13B:
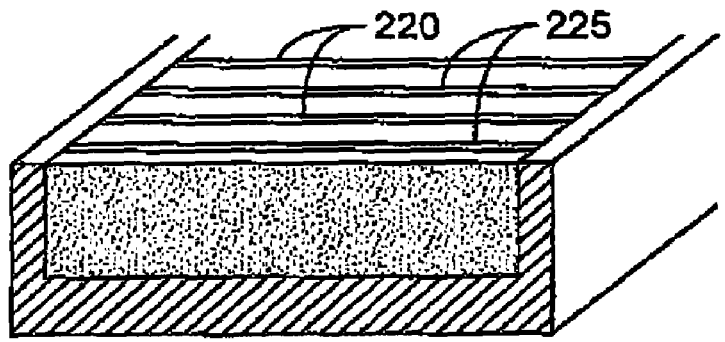
FIG. 13B is a sectional view of a Type "B" jaw similar to that of FIG. 13A with a plurality of opposing polarity electrodes with intermediate conductive-resistive matrices in the engagement surface in a different angular orientation.
Figure 13C:
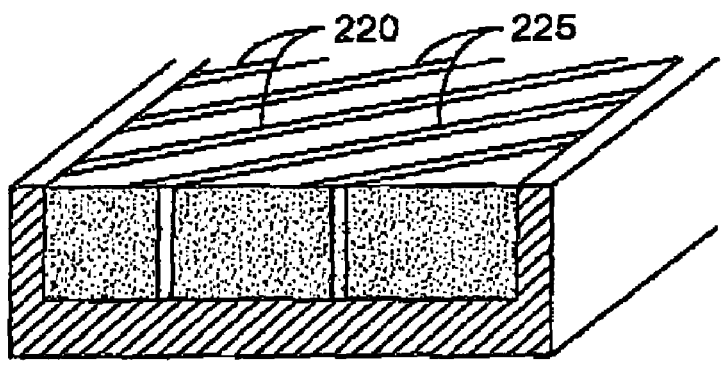
FIG. 13C is a sectional view of another Type "B" jaw similar to that of FIGS. 13A–13B with a plurality of opposing polarity electrodes with intermediate matrices in another angular orientation.

The jaw assembly also can carry a plurality of alternating opposing polarity electrode portions 220 and 225 with intermediate conductive-resistive matrix portions CM in any longitudinal, diagonal or transverse arrangements as shown in FIGS. 13A–13C. Any of these arrangements of electrodes and intermediate conductive-resistive matrix will function as described below at a reduced scale—with respect to any paired electrodes and intermediate matrix CM.

Figure 14A:
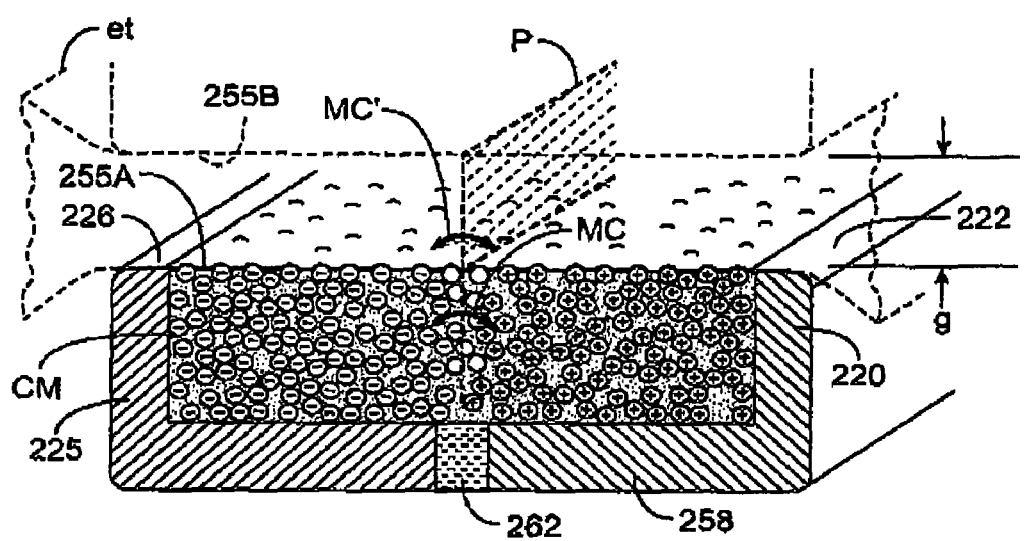
FIGS. 14A–14C graphically illustrate a method of the invention in causing a wave of Rf energy density to propagate across and engaged tissue membrane to denature tissue constituents.
Figure 14B:
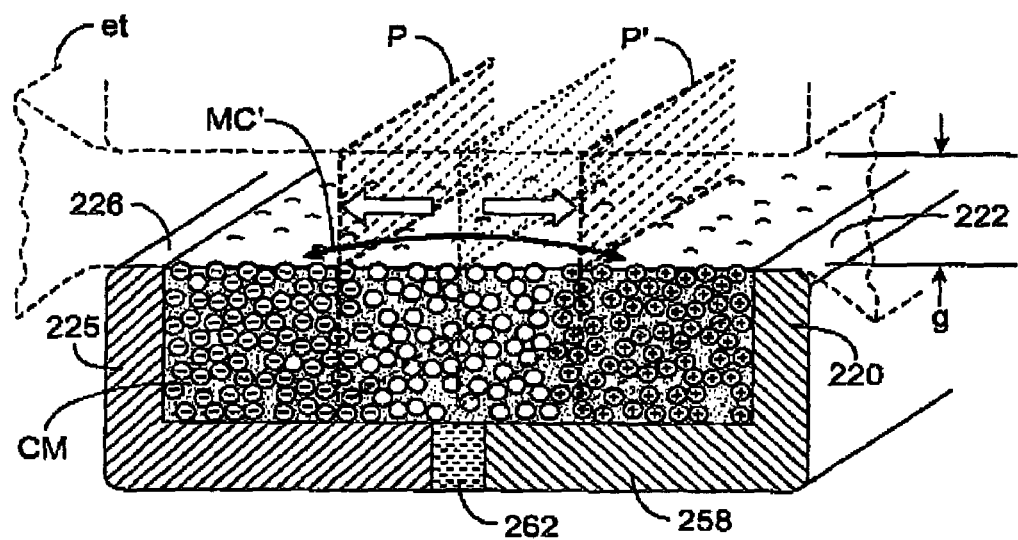
Figure 14C:
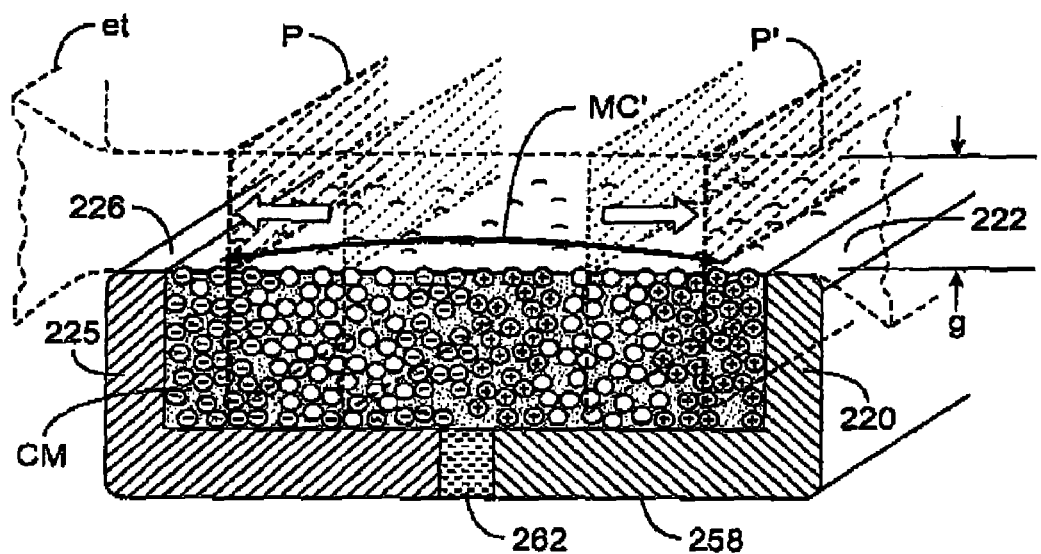

FIGS. 14A–14C illustrate sequential views of the method of using of the engagement surface layer of FIG. 11 to practice the method of the invention as relating to the controlled application of energy to tissue. For clarity of explanation, FIGS. 14A–14C depict exposed electrode surface portions 220 and 225 at laterally spaced apart locations with an intermediate resistive matrix CM that can create a "wave" or "front" of ohmic heating to sweep across the engaged tissue et. In FIG. 14A, the upper jaw 212B and engagement surface 250B is shown in phantom view, and comprises an insulator 252. The gap dimension g is not to scale, as described previously, and is shown with the engaged tissue having a substantial thickness for purposes of explanation.

FIG. 14A provides a graphic illustration of the matrix CM within engagement surface layer 250A at time $T_1$—the time at which electrical potential of a first polarity (indicated at +) is applied to electrode 220 via an electrical lead from voltage source 180 and controller 182. In FIGS. 14A–14C, the spherical graphical elements 162 of the matrix are not-to-scale and are intended to represent a "region" of conductive particles within the non-conductive elastomer 164. The graphical elements 162 thus define a polarity at particular microsecond in time just after the initiation of power application. In FIG. 14A, the body portion carrying electrode 225 defines a second electrical potential (−) and is coupled to voltage source 180 by an electrical lead. As can be seen in FIG. 14A, the graphical elements 162 are indicated as having a transient positive (+) or negative (−) polarity in proximity to the electrical potential at the electrodes. When the graphical elements 162 have no indicated polarity (see FIGS. 14B & 14C), it means that the matrix region has been elevated to a temperature at the matrix' switching range wherein electrical conductance is limited, as illustrated in that positively sloped temperature-resistance curve of FIG. 6 and the graphical representation of FIG. 8B.

As can be seen in FIG. 14A, the initiation of energy application at time $T_1$ causes microcurrents mc within the central portion of the conductive matrix CM as current attempts to flow between the opposing polarity electrodes 220 and 225. The current flow within the matrix CM in turn localizes corresponding microcurrents mc' in the adjacent engaged tissue et. Since the matrix CM is engineered to conduct electrical energy thereacross between opposing polarities at about the same rate as tissue, when both the matrix and tissue are at about 37° C., the matrix and tissue initially resemble each other, in an electrical sense. At the initiation of energy application at time $T_1$, the highest Rf energy density can be defined as an "interface" indicated graphically at plane P in FIG. 14A, which results in highly localized ohmic heating and denaturation effects along that interface which extends from the matrix CM into the engaged tissue. Thus, FIG. 14A provides a simplified graphical depiction of the interface or plane P that defines the "non-random" localization of ohmic heating and denaturation effects—which contrasts with all prior art methods that cause entirely random microcurrents in engaged tissue. In other words, the interface between the opposing polarities wherein active Rf heating is precisely localized can be controlled and localized by the use of the matrix CM to create initial heating at that central tissue location.

Still referring to FIG. 14A, as the tissue is elevated in temperature in this region, the conductive-resistive matrix CM in that region is elevated in temperature to its switching range to become substantially non-conductive (see FIG. 6) in that central region.

FIG. 14B graphically illustrates the interface or plane P at time $T_2$—an arbitrary microsecond or millisecond time interval later than time $T_1$. The dynamic interface between the opposing polarities wherein Rf energy density is highest can best be described as planes P and P' propagating across the conductive-resistive matrix CM and tissue that are defined by "interfaces" between substantially conductive and non-conductive portions of the matrix—which again is determined by the localized temperature of the matrix. Thus, the microcurrent mc' in the tissue is indicated as extending through the tissue membrane with the highest Rf density at the locations of planes P and P'. Stated another way, the system creates a front or wave of Rf energy density that propagates across the tissue. At the same time that Rf density (ohmic heating) in the localized tissue is reduced by the adjacent matrix CM becoming nonconductive, the matrix CM will begin to apply substantial thermal effects to the tissue by means of passive conductive heating as described above.

FIG. 14C illustrates the propagation of planes P and P' at time $T_3$—an additional arbitrary time interval later than $T_2$. The conductive-resistive matrix CM is further elevated in temperature behind the interfaces P and P' which again causes interior matrix portions to be substantially less conductive. The Rf energy densities thus propagate further outward in the tissue relative to the engagement surface 255A as portions of the matrix change in temperature. Again, the highest Rf energy density will occur at generally at the locations of the dynamic planes P and P'. At the same time, the lack of Rf current flow in the more central portion of matrix CM can cause its temperature to relax to thus again make that central portion electrically conductive. The increased conductivity of the central matrix portion again is indicated by (+) and (−) symbols in FIG. 14C. Thus, the propagation of waves of Rf energy density will repeat itself as depicted in FIGS. 14A–14C which can effectively weld tissue.

Using the methods described above for controlled Rf energy application with paired electrodes and a conductive-resistive matrix CM, it has been found that time intervals ranging between about 500 ms and 4000 ms can be sufficient to uniformly denature tissue constituents re-crosslink to from very strong welds in most tissues subjected to high compression. Other alternative embodiments are possible that multiply the number of cooperating opposing polarity electrodes 220 and 225 and intermediate or surrounding matrix portions CM.

Figure 15:
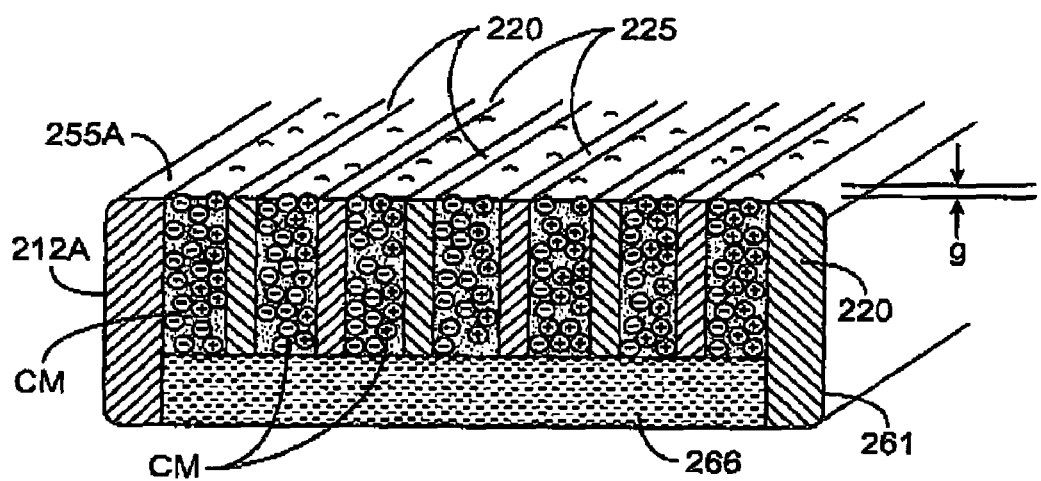
FIG. 15 is an enlarged sectional view of the exemplary jaw structure of FIG. 13A with a plurality of opposing polarity conductors on either side of conductive-resistive matrix portions.

FIG. 15 depicts an enlarged view of the alternative Type "B" jaw 212A of FIG. 13A wherein the engagement surface 250A carries a plurality of exposed conductive matrix portions CM that are intermediate a plurality of opposing polarity electrode portions 220 and 225. This lower jaw 212A has a structural body that comprises the electrodes 220 and 225 and an insulator member 266 that provide the strength required by the jaw. An insulator layer 261 again is provided on outer surfaces of the jaw excepting the engagement surface 255A. The upper jaw (not shown) of the jaw assembly can comprise an insulator, a conductive-resistive matrix, an active electrode portion or a combination thereof. In operation, it can be easily understood that each region of engaged tissue between each exposed electrode portion 222 and 226 will function as described in FIGS. 14A–14C.

The type of engagement surface 250A shown in FIG. 15 can have electrode portions that define an interior exposed electrode width ew ranging between about 0.005" and 0.20" with the exposed outboard electrode surface 222 and 226 having any suitable dimension. Similarly, the engagement surface 250A has resistive matrix portions that portions that define an exposed matrix width mw ranging between about 0.005" and 0.20".

Figure 16:
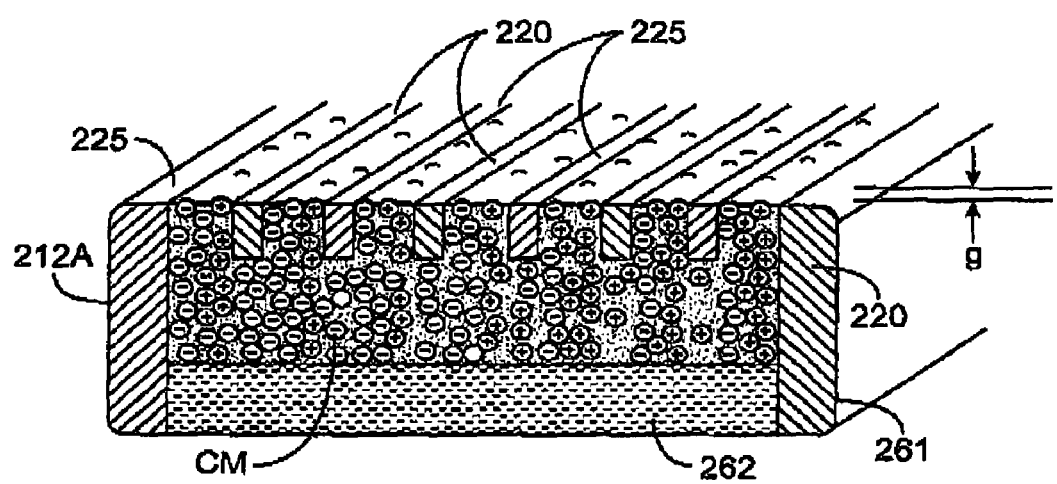
FIG. 16 is a sectional view of a jaw structure similar to that of FIG. 15 with a plurality of opposing polarity conductors that float within an elastomeric conductive-resistive matrix portions.

In the embodiment of FIG. 15, the electrode portions 220 and 225 are substantially rigid and extend into contact with the insulator member 266 of the jaw body thus substantially preventing flexing of the engagement surface even though the matrix CM may be a flexible silicone elastomer. FIG. 16 shows an alternative embodiment wherein the electrode portions 220 and 225 are floating within, or on, the surface layers of the matrix 250A.

Figure 17:
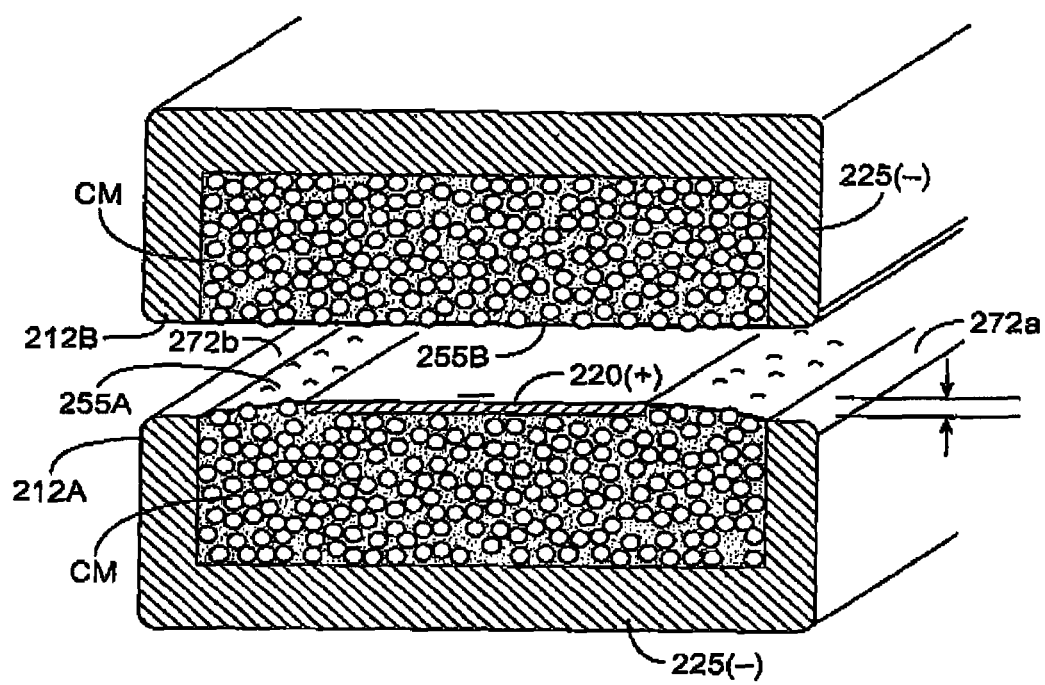
FIG. 17 is a sectional view of a jaw structure similar to that of FIG. 16 with a single central conductor that floats on a convex elastomeric conductive-resistive matrix with opposing polarity conductors in outboard locations.
Figure 18A:
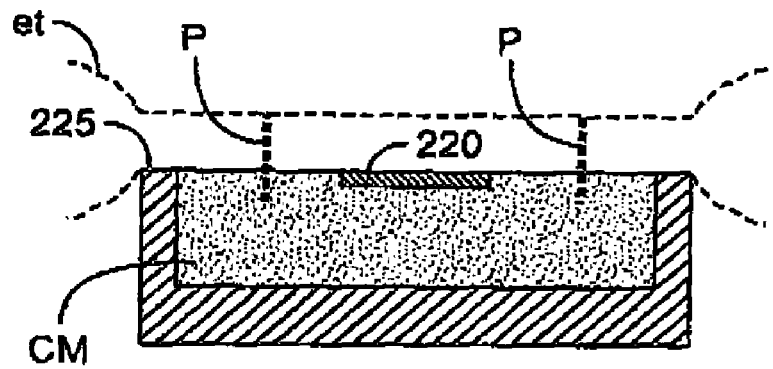
FIGS. 18A–18C provide simplified graphic views of the method of causing a wave of Rf energy density in the embodiment of FIG. 17, similar to the method shown in FIGS. 14A–14C.
Figure 18B:
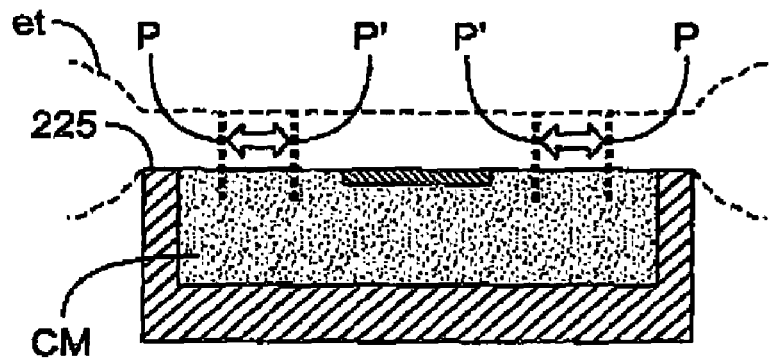
Figure 18C:
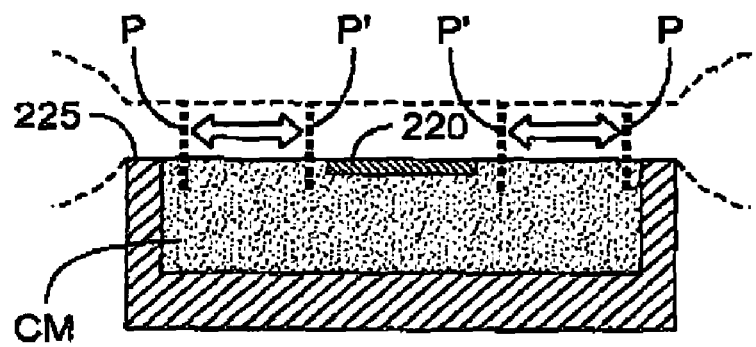

FIG. 17 illustrates an alternative Type "B" embodiment that is adapted for further increasing passive heating of engaged tissue when portions of the matrix CM are elevated above its selected switching range. The jaws 212A and 212B and engagement surface layers 255A and 255B both expose a substantial portion of matrix to the engaged tissue. The elastomeric character of the matrix can range between about 20 and 95 in the Shore A scale or above about 40 in the Shore D scale. Preferably, one or both engagement surface layers 255A and 255B can be "crowned" or convex to insure that the elastomeric matrices CM tend to compress the engaged tissue. The embodiment of FIG. 17 illustrates that a first polarity electrode 220 is a thin layer of metallic material that floats on the matrix CM and is bonded thereto by adhesives or any other suitable means. The thickness of floating electrode 220 can range from about 1 micron to 200 microns. The second polarity electrode 225 has exposed portions 272a and 272b at outboard portions of the engagement planes 255A and 255B. In operation, the jaw structure of FIG. 17 creates controlled thermal effects in engaged tissue by several different means. First, as indicated in FIGS. 18A–18C, the dynamic waves of Rf energy density are created between the opposing polarity electrode portions 220 and 225 and across the intermediate matrix CM exactly as described previously. Second, the electrically active components of the upper jaw's engagement surface layer 255B cause microcurrents between the engagement surface layers 255A and 255B, as well as to the outboard exposed electrode surfaces exposed portions 272a and 272b, between any portions of the matrices that are below the selected switching range. Third, the substantial volume of matrix CM is each jaw provides substantial heat capacity to very rapidly cause passive heating of tissue after active tissue heating is reduced by increasing impedance in the engaged tissue et.

Figure 19:
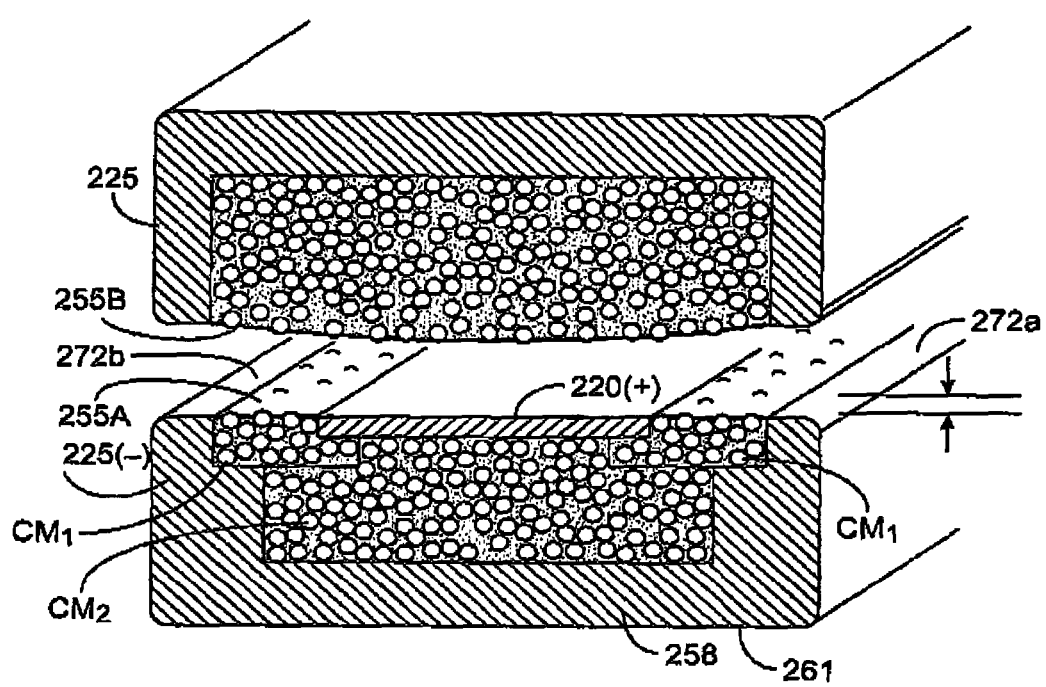
FIG. 19 is a sectional view of another exemplary jaw structure that carries two conductive-resistive matrix portions, each having a different durometer and a different temperature coefficient profile.

FIG. 19 illustrates another Type "B" embodiment of jaws structure that again is adapted for enhanced passive heating of engaged tissue when portions of the matrix CM are elevated above its selected switching range. The jaws 212A and 212B and engagement surface layers 255A and 255B again expose matrix portions to engaged tissue. The upper jaw's engagement surface layer 255B is convex and has an elastomeric hardness ranging between about 20 and 80 in the Shore A scale and is fabricated as described previously.

Of particular interest, the embodiment of FIG. 19 depicts a first polarity electrode 220 that is carried in a central portion of engagement plane 255A but the electrode does not float as in the embodiment of FIG. 17. The electrode 220 is carried in a first matrix portion $CM_1$ that is a substantially rigid silicone or can be a ceramic positive temperature coefficient material. Further, the first matrix portion $CM_1$ preferably has a differently sloped temperature-resistance profile (cf. FIG. 6) that the second matrix portion $CM_2$ that is located centrally in the jaw 212A. The first matrix portion $CM_1$, whether silicone or ceramic, has a hardness above about 90 in the Shore A scale, whereas the second matrix portion $CM_2$ is typically of a silicone as described previously with a hardness between about 20 and 80 in the Shore A scale. Further, the first matrix portion $CM_1$ has a higher switching range than the second matrix portion $CM_2$. In operation, the wave of Rf density across the engaged tissue from electrode 220 to outboard exposed electrode portions 272a and 272b will be induced by matrix $CM_1$ having a first higher temperature switching range, for example between about 70° C. to 80° C., as depicted in FIGS. 18A–18C. The rigidity of the first matrix $CM_1$ prevents flexing of the engagement plane 255A. During use, passive heating will be conducted in an enhanced manner to tissue from electrode 220 and the underlying second matrix $CM_2$ which has a second selected lower temperature switching range, for example between about 60° C. to 70° C. This Type "B" system has been found to be very effective for rapidly welding tissue—in part because of the increased surface area of the electrode 220 when used in small cross-section jaw assemblies (e.g., 5 mm. working ends).

Figure 20:
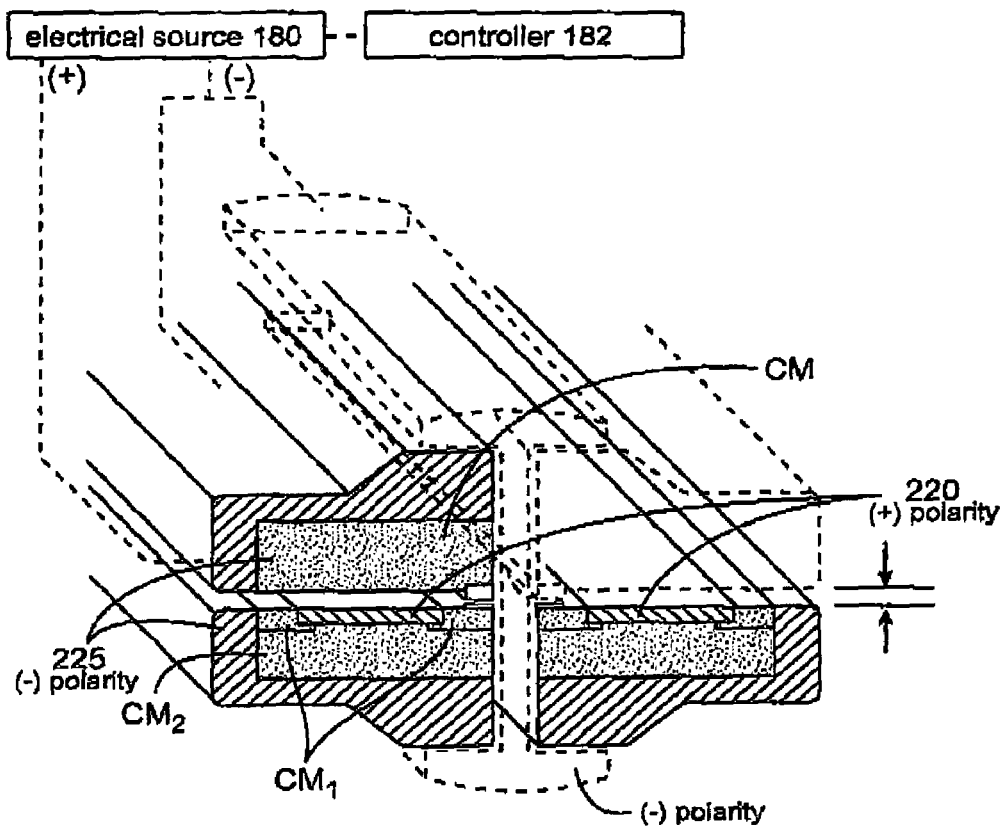
FIG. 20 is a sectional view of a jaw assembly having the engagement plane of FIG. 17 carried in a transecting-type jaws similar to that of FIGS. 3A–3B.

FIG. 20 shows the engagement plane 255A of FIG. 17 carried in a transecting-type jaws assembly 200D that is similar to that of FIGS. 3A–3B. As described previously, the Type "B" conductive-resistive matrix assemblies of FIGS. 12–19 are shown in a simplified form. Any of the electrode-matrix arrangements of FIGS. 12–19 can be used in the cooperating sides of a jaw with a transecting blade member-similar to the embodiment shown in FIG. 20.

Figure 21:
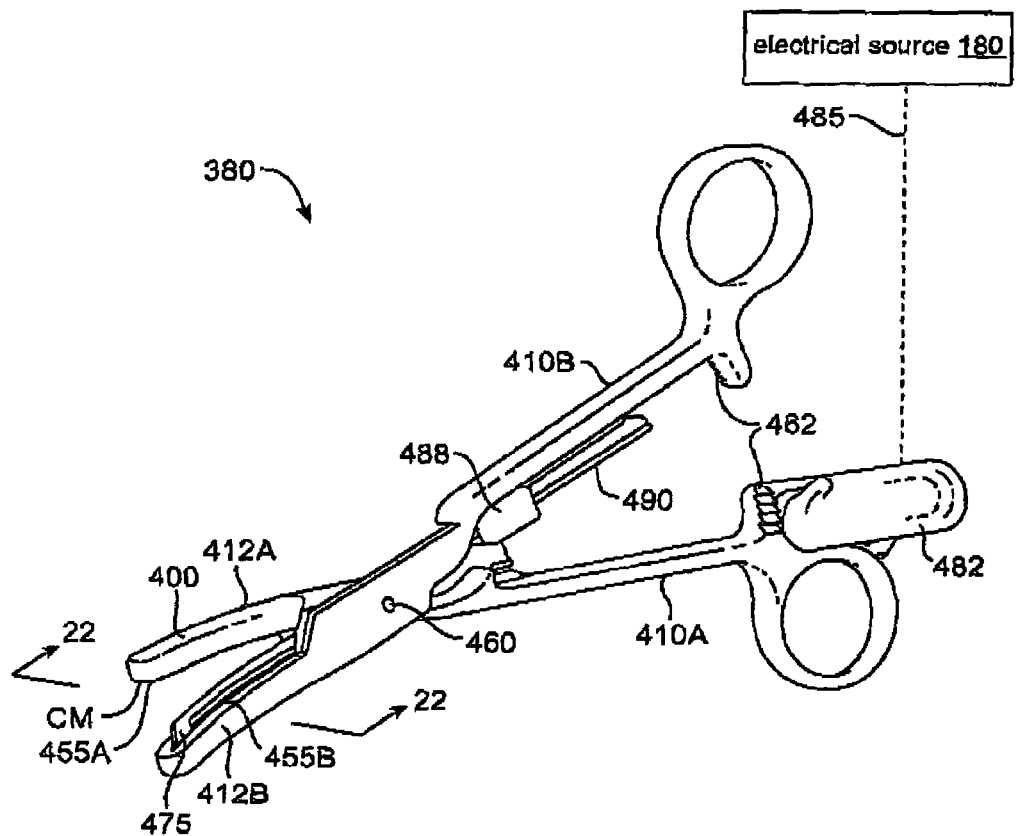
FIG. 21 is a perspective view of a Type "C" scissor-type instrument with a jaw structure similar to Types "A"–"B" embodiments with (i) a disposable cartridge that carries a conductive-resistive matrix system according to the invention and (ii) a disposable cartridge that carries a transecting knife blade (shown in an extended position).
Figure 22:
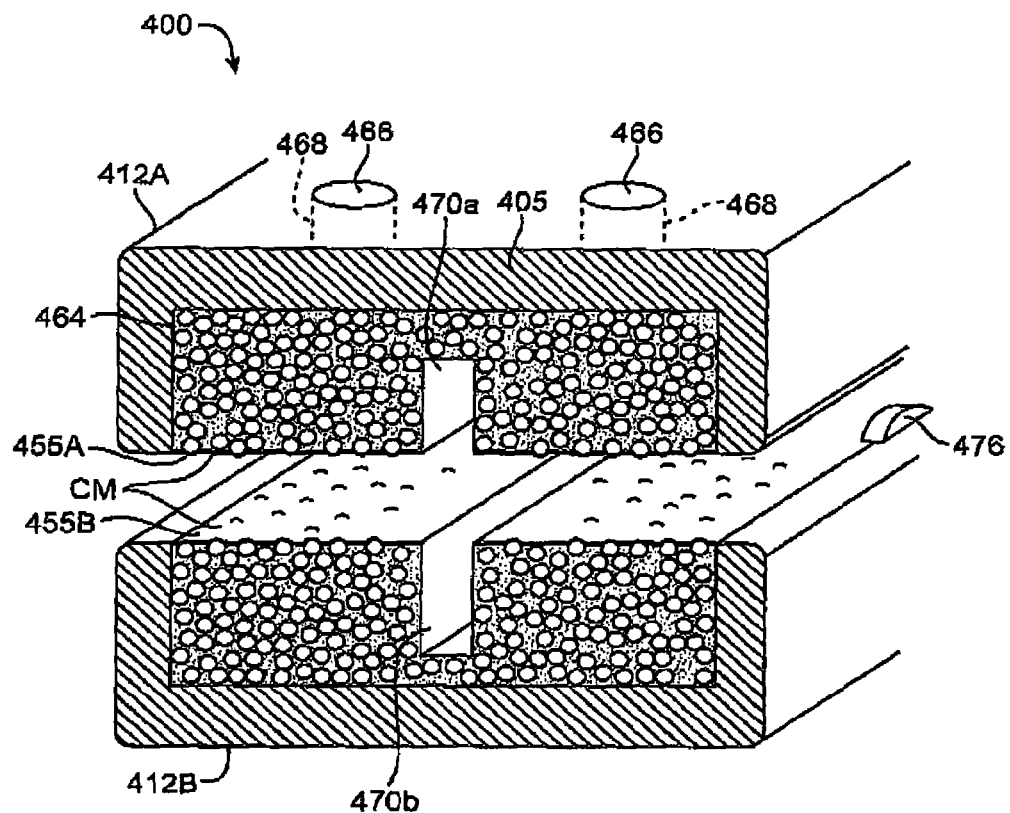
FIG. 22 is a sectional view of the working end of the opposing jaws and conductive-resistive matrix system of FIG. 21 taken along line 22—22 of FIG. 21.
Figure 23:
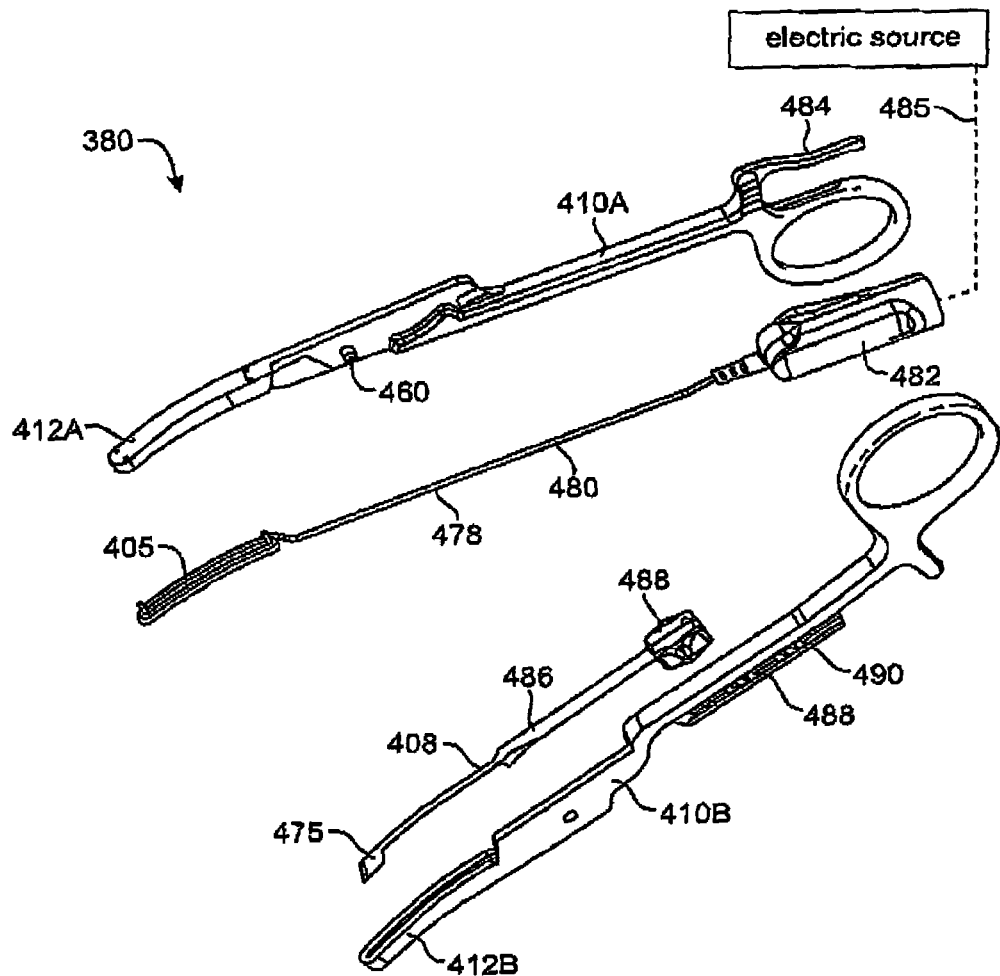
FIG. 23 is an exploded view of the components of the Type "C" scissor-type instrument of FIG. 21 with the disposable electrosurgical cartridge and the disposable blade cartridge de-mated form the scissor arms.

3. Type "C" system for tissue welding. FIGS. 21 and 22 illustrate an scissor-type instrument 380 corresponding to the invention having an exemplary Type "C" jaw assembly 400 that carries a conductive-resistive matrix CM that comprises a variably resistive body as described previously for (i) controlling Rf energy density and microcurrent paths in engaged tissue, and (ii) for contemporaneously controlling passive conductive heating of the engaged tissue. The variably resistive body or matrix extends inwardly from the tissue-engaging surface as described above. The scissor-type instrument is useful in that it provides very rapid tissue welding capabilities in an instrument form that is commonly used in open surgeries. In one preferred embodiment, the scissor-type instrument 380 can be fitted with a blade for transecting welded tissue. Of particular interest, the scissor body of the instrument can be reusable with (i) a disposable electrosurgical cartridge 405 and (ii) a disposable blade cartridge 408 (FIG. 23). The blade cartridge 408 provides and thin flexible cutting blade that can be moved between a first retracted position and a second extended position.

In FIGS. 21 and 22, it can be seen that first and second scissor arm members 410A and 410B carry opposing first and second jaws 412A and 412B that define respective tissue-engaging surfaces 455A and 455B. In this embodiment, the upper jaw 412A and engagement surface 455A are similar to that described in the embodiments of FIG. 20 with a conducive-resistive matrix CM coupled to a voltage source 180 as described previously. The lower jaw's engagement surface 455B can carry a variably resistive matrix as in FIG. 20, a return electrode as in FIGS. 5 and 7A, or can be fully insulated as described in the embodiment of FIGS. 14A–14C. The scissor jaw arms 410A and 410B rotate about pivot 460 (FIG. 21).

The scissor-type instrument 380 of FIG. 21 provides jaw working ends that are in a curved configuration but the jaw portions also can be linear. Such an instrument can apply substantial leverage on the engagement surfaces to thereby apply very high compressive forces on the engaged tissue and thus function optimally to create an effective weld as described above. The handle portion of the scissor jaw arms 410A and 410B provides a ratchet-type lock-release mechanism 462 for clamping the jaws closed as is common in the art.

Of particular interest, referring to FIGS. 22 and 23, the re-usable instrument has a replaceable, disposable cartridge 405 that carries a conductive-resistive matrix CM. FIG. 23 shows the cartridge 405 de-mated from the scissor arm 410A and indicates how the cartridge fits into a recessed receiving portion 464 of upper jaw 412A. At least one pin or projecting element 466 cooperates with openings 468 in the jaw portion (see FIG. 22) to insure that the cartridge is positioned properly and locked in place. In the embodiment shown in FIGS. 21–23, the cartridge 405 has an axial channel or slot 470a therein that cooperates with an optional slidable blade element 475. As can be seen in FIG. 22, when the jaws carry opposing polarity exposed electrodes or conductive matrices CM, at least one jaw carries an insulated projecting element 476 along an edge of the jaw (or along an edge of the central blade channel) to prevent the opposing polarity components from contacting one another when the jaws are in the closed position.

The cartridge 405 has an electrical lead 478 with and insulative coating 480 that extends proximally to connector 482 that clips on to a cooperating member 484 of the scissor arm (FIG. 23). An electrical cable 485 extending from the voltage source 180 couples to the connector 482 to provide Rf energy to the instrument.

In the type of instrument shown in FIG. 21, the upper jaw portion 412A carries the conductive-resistive matrix cartridge 405 that cooperates the engagement surface 455B of the lower jaw portion 412B. In a preferred embodiment as shown in FIG. 22, the lower jaw portion 412B carries a cooperating variably resistive matrix CM of the type shown in FIGS. 19 and 20. As can be seen in FIG. 22, the conductive-resistive matrix CM in the lower jaw's engagement surface 455B has an axial channel or slot 470b therein that receives the slidable blade element 475. The conductive-resistive matrix CM of the lower scissor jaw can be adapted to be a permanent component that is sterilizable and that does not require replacement after each use. Alternatively, the conductive-resistive matrix CM of the lower scissor jaw can be made to be a disposable cartridge. In the embodiments that require electrical functionality in each jaw, the leads or leads from the voltage source 180 can be carried from the first scissor arm 410A to the second scissor arm 410B across the pivot pin 460 as is known the art so that the cable 485 from the voltage source 180 needs to be coupled to only one scissor arm.

FIG. 23 also shows the instrument 380 with a de-mated disposable blade cartridge 408 that can be snap-fit into the second scissor arm 410B. The disposable blade cartridge 408 has a flexible blade element 475 coupled to a medial shaft portion 486 that carries a plastic grip member 488 at is proximal end. The blade cartridge 408 is fabricated so that the medial shaft portion 486 is releasably and slidably locked into a cooperated slot 490 in a member 492 carried by the second scissor arm 410B.

The instrument 380 of FIGS. 21 and 23 further includes a safety features that comprise first and second interlocks as are known in the art. The first interlock built into the blade cartridge 408 and the scissor arms 410A and 410B allows the blade 475 to slide distally to its second extended position in the jaw portions only when the scissor arms and jaws are rotated to the second closed position. The second safety interlock mechanism built into blade cartridge 408 and the scissor arms prevents the rotation of the scissor arms to the first open position at any time the blade 475 to is still in its second extended position. Only after the blade 475 is moved back to its first retracted position can the scissor arms be opened.

Figure 24:
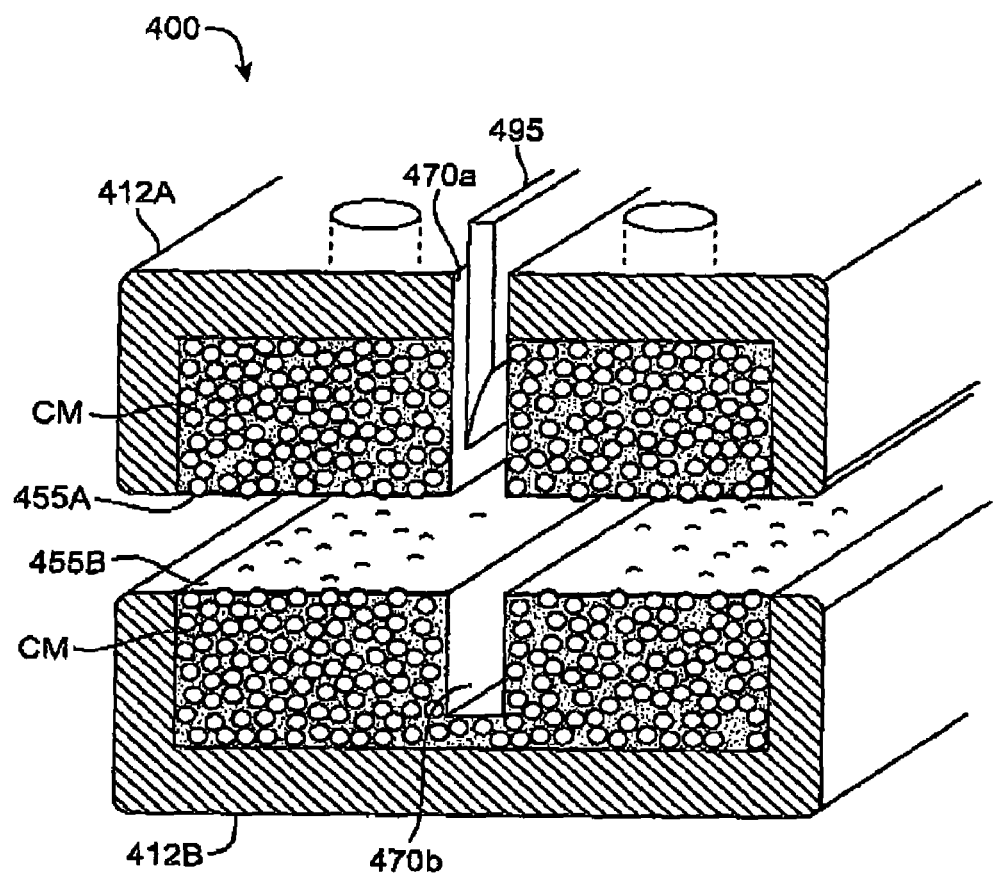
FIG. 24 is an alternative embodiment of a Type "C" scissor-type jaw structure similar to that of FIG. 21 except carrying a rotatable blade element.

In another embodiment shown in FIG. 24, it should be appreciated that the cutting blade element need not be a reciprocating blade 475 as shown in FIGS. 21–23. Rather, FIG. 24 illustrates that a scissor-type blade element 495 that rotates with the scissor arm 410A can be provided. It can easily be understood that the blade element 495 can be adapted to automatically rotate fully into the blade slots 470a and 470b to cut the tissue after the engagement surfaces 455A and 455B clamp against the tissue. Alternatively, an interlock can be provided to only rotate the blade to cut the tissue after the tissue is welded and the physician elects to transect the tissue by rotating the blade to cut the tissue.

In another embodiment corresponding to the invention, the electrosurgical working end carries an exposed electrical lead portion that extends to the electrode or conductive-resistive matrix CM. For example, the instrument 380 of FIG. 21 has exposed electrical lead 480. It should be appreciated that the scope of the invention extends to any medical device working end. It has been found that visual signals may be the optimal means of informing a physician intraoperatively of the status of energy delivery to tissue, whether in an endoscopic or open surgery. For example, audio tones are often used to alert the physician as to on/off energy delivery modes.

In another embodiment (not shown) a scissor-type instrument similar to that of FIG. 21 can have a first jaw portion that is adapted to receive an electrosurgical cartridge and a second jaw that has permanent blade. The blade can have a first recessed position wherein the jaws' engagement surfaces can be locked to together and a second exposed position wherein the scissor arm are closed further to cause the blade to cross the plane between the engagement surfaces to cut the tissue.

Figure 25:
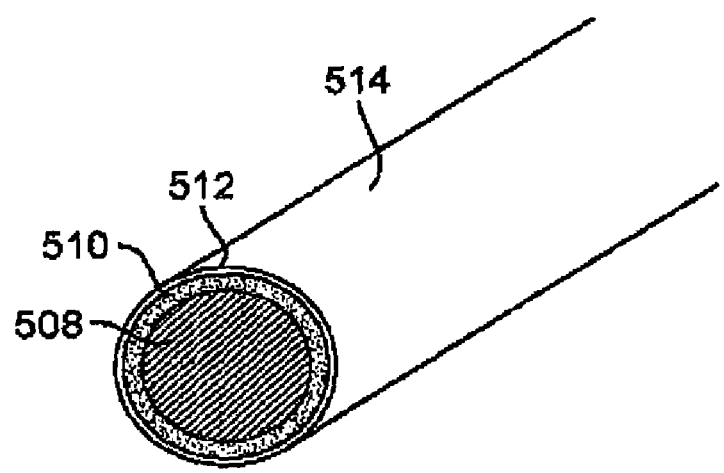
FIG. 25 is an electrical lead or cable of an electrosurgical instrument that carries a thermochromic layer for providing a visual indicator to the physician.

Referring to FIG. 25, the present invention provides an electrical lead 504 with series of layers that collectively provide an insulative coating that changes from a first color to a second "signal" color when electrical current is flowing through the lead 504. Alternatively, the lead can change between a range of colors that can indicate to a significant extent the impedance of the engaged tissue. The electrical lead can be an exposed wire lead 478 as shown in FIGS. 23 and 25 or it can be a thin film conductor element 508 laminated on a surface of the instrument as depicted in FIG. 26.

Figure 26:
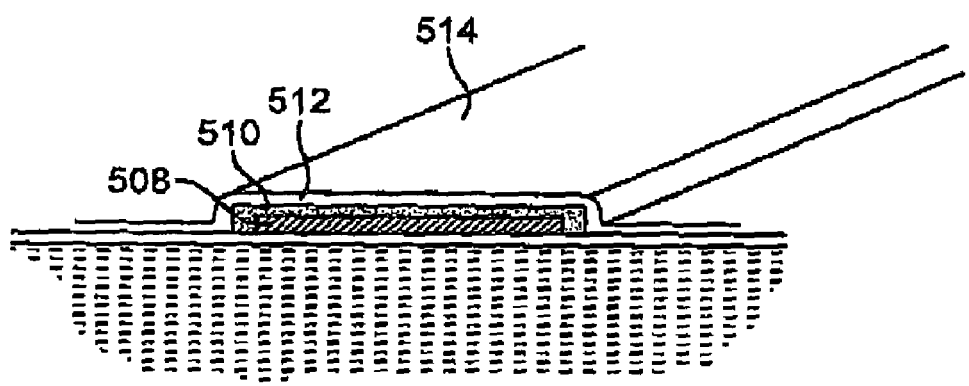
FIG. 26 is an alternative flex circuit electrical lead of an electrosurgical instrument that carries a thermochromic layer for providing a visual indicator to the physician.

In one exemplary inexpensive printed and laminated embodiment, as shown in FIG. 26, the invention comprises a conductor element 508 with a thin conductive-resistive matrix 510 (or a conductive ink) printed over the conductor 508. A thermochromic ink layer 512 is then printed over the conductor 508 and matrix 510. A thermochromic ink can be engineered to undergo a thermochromic transition and change its color after it reaches a selected temperature. A final insulative transparent layer 514 is applied over the thermochromic layer 512, or more preferably the thermochromic composition is integrated into the insulator layer. By applying such layers over a substrate, it is possible to create an extremely inexpensive printed component (e.g., a flex circuit component) that changes in temperature depending on the amount of electricity transmitted through the lead which heats the matrix and then causes a reversible thermochromic transition in layer 512 at a selected temperature. The conductor element 508 can be coverer by either a positive or negative temperature coefficient matrix 510 that defines a selected switching range to cause current to reach the thermochromic layer, with an optional second layer of an opposing polarity conductor to thus engineer the thermochromic layer 512 to change color at any selected event that would provide useful information to the physician, such as a change in temperature, a change in current flow, a change impedance in the engaged tissue, or a short circuit in the system.

FIG. 25 shows similar layers of cable-type conductor element 508, conductive-resistive matrix 510 and thermochromic layer 512 in the form of a round wire lead that can function as described above. Co-pending U.S. patent application Ser. No. 10/441,519 filed May 20, 2003 titled "Electrosurgical Working End with Thermochromic or Piezochromic Indicators", incorporated herein by reference, provides further disclosures of thermochromic compositions in a coating about the surface of a working end to indicate temperature.

There are two types of thermochromic ink: liquid crystal and leucodye types. A liquid crystal based thermochromic ink is sensitive to very small changes in temperature. Leucodyes are specially formulated substances that change from a specific color to a clear state when subjected to a temperature change of about 5 degrees F. or more. Thermochromic inks can be formulated to change color at specific temperatures, which can be selected along with the matrix resistance characterstics as described above. The thermochromic portion of the lead is typically in the working end, but also can be in the handle or medial introducer portion of the instrument.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A bipolar electrosurgical instrument, the instrument comprising:
a working end having first and second openable-closeable jaws having first and second respective tissue-engaging surfaces for engaging tissue and first and second respective support structures;
the first tissue-engaging surface comprising a portion of the first support structure and a polymeric body, the first support structure configured as a first polarity electrode and at least partially surrounding the polymeric body, the polymeric body having a transverse cross section comprising a significant fractional area of a transverse cross section of the first jaw, the polymeric body having a non-linear positively sloped temperature resistance profile in a selected tissue treatment range; and
the second tissue-engaging surface comprising a second polarity electrode.

2. The bipolar electrosurgical instrument of claim 1, wherein the second tissue-engaging surface further comprises a portion of the second support structure.

3. The bipolar electrosurgical instrument of claim 2, wherein the second tissue-engaging surface further comprises another polymeric body, the other polymeric body extending inwardly from the second tissue-engaging surface and having a transverse cross section comprising a significant fractional area of a transverse cross section of the second jaw, the other polymeric body having a non-linear positively sloped temperature resistance profile in a selected tissue treatment range.

4. The bipolar electrosurgical instrument of claim 3, wherein the second support structure at least partially surrounds the other polymeric body.

5. The bipolar electrosurgical instrument of claim 3, wherein the second support structure is configured as a first polarity electrode.

6. A bipolar electrosurgicul instrument, the instrument comprising:
a working end having first and second openable-closeable jaws comprising first and second respective tissue-engaging surfaces for engaging tissue and first and second respective support structures, the first tissue-engaging surface comprising a first polarity electrode, the second tissue-engaging surface comprising a second polarity electrode; and
a polymeric body extending inwardly from the second tissue-engaging surface and partially surrounded by the second support structure, the polymeric body having a transverse cross section comprising a significant fractional area of a transverse cross section of the second jaw, the second jaw transverse cross section comprising a support structure cross section and the polymeric body cross section, the polymeric body having a non-linear positively sloped temperature resistance profile defining a temperature treatment range for welding tissue.

7. The bipolar electrosurgical instrument of claim 6, wherein the first tissue-engaging surface further comprises a second polarity electrode.

8. The bipolar electrosurgical instrument of claim 6, further comprising:
another polymeric body extending inwardly from the first tissue-engaging surface, the another polymeric body having a transverse cross section comprising a significant fractional area of a transverse cross section of the first jaw, the first jaw transverse cross section comprising a support structure cross section and the another polymeric body cross section, the other polymeric body having a non-linear positively sloped temperature resistance profile defining a temperature treatment range for welding tissue.

* * * * *